(12) United States Patent
McKenzie et al.

(10) Patent No.: US 8,097,430 B2
(45) Date of Patent: Jan. 17, 2012

(54) ANTIGEN TARGETING

(75) Inventors: Brent McKenzie, Upwey (AU); Jefferey Boyle, Heidelberg (AU); Andrew Lew, Essendon (AU)

(73) Assignee: The Council of Queensland Institute of Medical Research, Queensland (AU)

( * ) Notice: Subject to any disclaimer, the term of this patent is extended or adjusted under 35 U.S.C. 154(b) by 1036 days.

(21) Appl. No.: 10/476,313

(22) PCT Filed: May 24, 2002

(86) PCT No.: PCT/AU02/00661
§ 371 (c)(1),
(2), (4) Date: Jun. 23, 2004

(87) PCT Pub. No.: WO02/096949
PCT Pub. Date: Dec. 5, 2002

(65) Prior Publication Data
US 2004/0241175 A1  Dec. 2, 2004

(30) Foreign Application Priority Data
May 25, 2001 (AU) ........................ PR5241

(51) Int. Cl.
*G01N 33/00* (2006.01)
*G01N 33/53* (2006.01)
*G01N 33/567* (2006.01)

(52) U.S. Cl. ........ 435/7.24; 435/7.1; 435/7.21; 514/837

(58) Field of Classification Search .................... 424/184
See application file for complete search history.

(56) References Cited

U.S. PATENT DOCUMENTS
2004/0023373 A1* 2/2004 Briskin ...................... 435/320.1

FOREIGN PATENT DOCUMENTS
| WO | WO 94/13312 | 6/1994 |
| WO | WO 96/24673 | 8/1996 |
| WO | WO 98/44129 | 10/1998 |
| WO | WO 99/43839 | 9/1999 |

OTHER PUBLICATIONS

McKenzie et al. Cholera toxin B subunit as a carrier protein to stimulate a mucosal immune response. J Immunol. Oct. 1984;133(4):1818-1824.*
Ogra et al. Vaccination strategies for mucosal immune responses. Clin Microbiol Rev. Apr. 2001; 14(2); 430-445.*
Quiding-Jarbrink et al Gut 2001, vol. 49 pp. 519-525.*
Zhou et al (Vaccine 1995 vol. 13 No. 7 pp. 637-644).*
Quiding-Jarbrink et al (Gut 2001, vol. 49 pp. 519-525).*
Holmgren et al., "Strategies for the Induction of Immune Responses at Mucosal Surfaces Surfaces Making Use of Cholera Toxin B Subunit as Immunogen, Carrier and Adjuvant" *Am. J. Trop. Med. Hyg.* 50(5):42-54 (1994).
Mestecky et al., "Routes of Immunization and Antigen Delivery Systems for Optimal Mucosal Immune Responses in Humans" *Behring Inst. Mitt.* 98:33-43 (1997).

* cited by examiner

*Primary Examiner* — Gary Nickol
*Assistant Examiner* — Jegatheesan Seharaseyon
(74) *Attorney, Agent, or Firm* — Karl Bozicevic; Bozicevic, Field & Francis LLP

(57) ABSTRACT

The present invention provides a method of raising an immune response in an animal. The method comprises administering to the animal a composition comprising a carrier and an antigen bound to a targeting moiety wherein the targeting moiety binds to at least one receptor present in circulatory vessels in Gut Associated Lymphoid Tissue. It is preferred that the targeting moiety binds to Mucosal Addressin Cellular Adhesion Molecule-1.

11 Claims, 11 Drawing Sheets

ANTIGEN TARGETING

FIELD OF THE INVENTION

The present invention to compositions and methods for raising an immune response in animals. In particular the compositions and methods of the present invention are useful in raising mucosal and systemic immunity.

BACKGROUND OF THE INVENTION

As the preferred site of entry or colonization for many pathogens, mucosal surfaces of the body play an important role in defence against numerous infections [1]. However, induction of mucosal immunity, other than by live oral vaccines, has been problematic. Physiochemical barriers at mucosal surfaces prevent adequate amounts of intact antigen reaching underlying mucosal lymphoid tissue and antigen localization in lymphoid tissues is critical for immune induction [2]. The small amount of antigen that does reach these lymphoid sites is largely ignored in a system set up to maintain non-reactivity or tolerance to a heavy burden of food and other benign antigens encountered daily.

Effective delivery of vaccine antigens to Gut Associated Lymphoid Tissue (GALT) has long been recognised as the primary hurdle for mucosal vaccine development. Strategies using the oral route impose a host of obstacles including mucus barriers, degradative gastric acid and alimentary enzymes [3,4]. To overcome this, co-delivery of antigen with adjuvants such as cholera toxin has been employed [5], but the clinical application is limited due to the toxicity of such adjuvants. Direct injection of antigen into mucosal lymphoid tissue has also been used [6,7], but such practices would be unlikely to be accepted by vaccinees.

The present inventors postulated that delivering antigens via the blood targeted to mucosal lymphoid tissues may bypass these obstacles. The present inventors tested targeting of antigens to the Mucosal Addressin Cellular Adhesion Molecule-1, (MAdCAM-1), a receptor present in circulatory vessels in the Gut Associated Lymphoid Tissue (GALT) and found that such antigen targeting induced a rapid mucosal IgA response in the gut and augmented (1000 fold) the systemic response to antigen.

SUMMARY OF THE INVENTION

Accordingly in a first aspect the present invention consists in a method of raising an immune response in an animal, the method comprising administering to the animal a composition comprising a carrier and an antigen bound to a targeting moiety wherein the targeting moiety binds to at least one receptor present in circulatory vessels in Gut Associated Lymphoid Tissue.

In a second aspect the present invention consists in a targeted antigen comprising an antigen bound to a targeting moiety wherein the targeting moiety binds to at least one receptor present in circulatory vessels in Gut Associated Lymphoid Tissue.

In a third aspect the present invention consists in an antigenic composition, the composition comprising a carrier and an antigen bound to a targeting moiety wherein the targeting moiety binds to at least one receptor present in circulatory vessels in Gut Associated Lymphoid Tissue.

In a fourth aspect the present invention consists in a method of raising an immune response in an animal, the method comprising administering to the animal a composition comprising a carrier and a DNA molecule, the DNA molecule encoding an antigen and a targeting moiety which binds to at least one receptor present in circulatory vessels in Gut Associated Lymphoid Tissue.

In a fifth aspect the present invention consists in a DNA molecule, the DNA molecule encoding an antigen and a targeting moiety which binds to at least one receptor present in circulatory vessels in Gut Associated Lymphoid Tissue.

In a sixth aspect the present invention consists in an antigenic composition, the composition comprising a carrier and a DNA molecule, the DNA molecule encoding an antigen and a targeting moiety which binds to at least one receptor present in circulatory vessels in Gut Associated Lymphoid Tissue.

In a preferred embodiment of the present invention the targeting moiety binds to Mucosal Addressin Cellular Adhesion Molecule-1.

DETAILED DESCRIPTION

Figure 1:
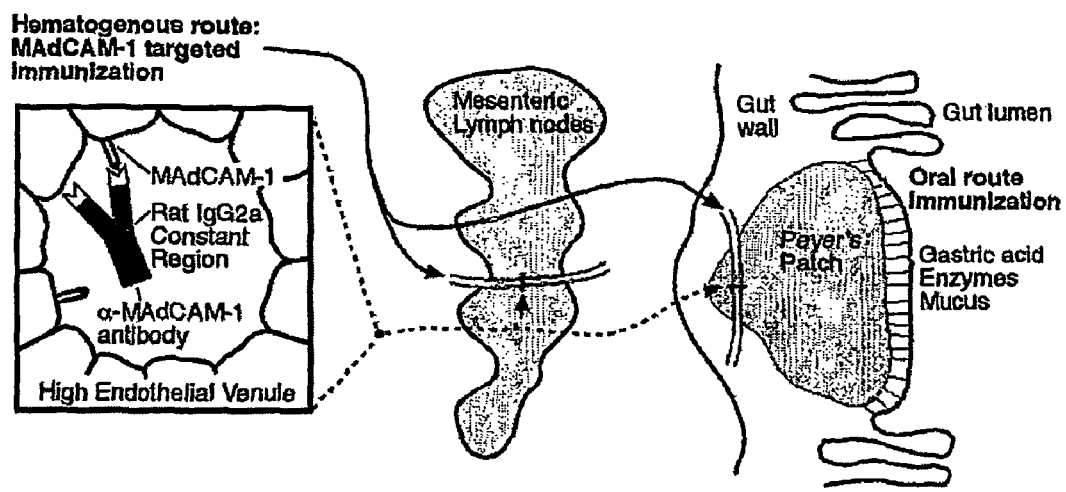
FIG. 1. Targeting mucosal inductive sites via the blood. a, Scheme of antigen targeting to MAdCAM-1. Rat IgG2a anti-MAdCAM-1 antibodies were used to target sites of MAdCAM-1 expression in mesenteric lymph nodes (MLN) and Peyer's patches (PP) of the GALT. Targeting these specialized lymphoid sites via the blood route bypasses physiochemical barriers associated with mucosal antigen delivery (via the oral route). b, MAdCAM-1 targeted antigen preferentially localizes to mucosal inductive sites in-vivo. Proteins were radioiodinated and injected intravenously (5 mice per group) to quantify the amount accumulated in mucosal versus peripheral lymphoid sites. Means and standard deviations are shown. Binding of anti-MAdCAM-1 antibody MECA-367 was enhanced in MLN and PP compared with the isotype control (p=*0.013 and **0.002 respectively; Student t-test). No such enhancement was found in peripheral lymphoid sites such as the spleen and inguinal lymph nodes (ILN).
Figure 1:
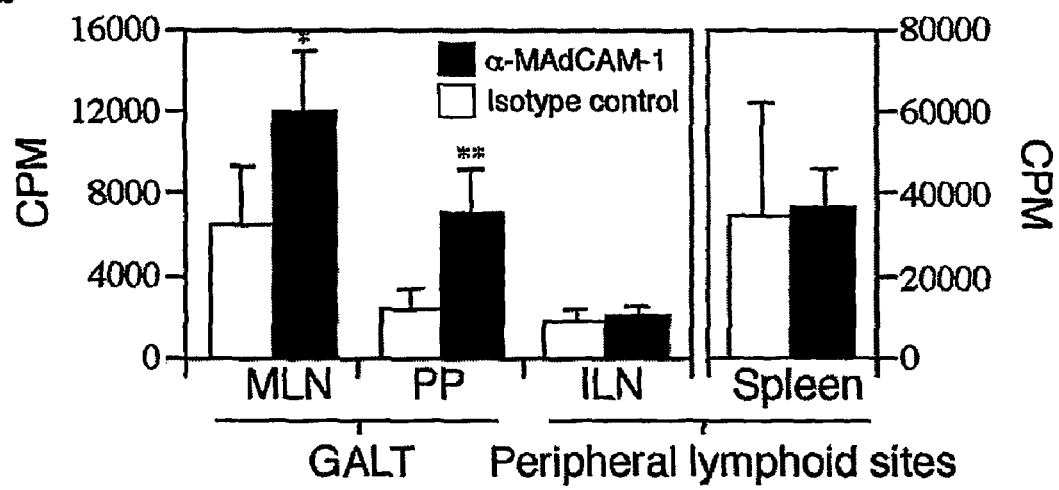

In a first aspect the present invention consists in a method of raising an immune response in an animal, the method comprising administering to the animal a composition comprising a carrier and an antigen bound to a targeting moiety wherein the targeting moiety binds to at least one receptor present in circulatory vessels in Gut Associated Lymphoid Tissue.

In a second aspect the present invention consists in a targeted antigen comprising an antigen bound to a targeting moiety wherein the targeting moiety binds to at least one receptor present in circulatory vessels in Gut Associated Lymphoid Tissue.

In a third aspect the present invention consists in an antigenic composition, the composition comprising a carrier and an antigen bound to a targeting moiety wherein the targeting moiety binds to at least one receptor present in circulatory vessels in Gut Associated Lymphoid Tissue.

In a preferred embodiment the composition is administered to the animal parenterally. Routes of administration include IV, IM, IP, subcutaneous and intradermal. It is preferred that the administration is by a haematogenous route.

In a fourth aspect the present invention consists in a method of raising an immune response in an animal, the method comprising administering to the animal a composition comprising a carrier and a DNA molecule, the DNA molecule encoding an antigen and a targeting moiety which binds to at least one receptor present in circulatory vessels in Gut Associated Lymphoid Tissue.

In a fifth aspect the present invention consists in a DNA molecule, the DNA molecule encoding an antigen and a targeting moiety which binds to at least one receptor present in circulatory vessels in Gut Associated Lymphoid Tissue.

In a sixth aspect the present invention consists in an antigenic composition, the composition comprising a carrier and a DNA molecule, the DNA molecule encoding an antigen and a targeting moiety which binds to at least one receptor present in circulatory vessels in Gut Associated Lymphoid Tissue.

In a preferred embodiment of the present invention the targeting moiety binds to Mucosal Addressin Cellular Adhesion Molecule-1.

Molecules which target MAdCAM-1 are known in the art. These include anti-MAdCAM-1 antibodies and alpha 4 and beta 7 integrins. It is presently preferred that the targeting moiety is an antibody, an antibody fragment or an antibody binding domain. Further information regarding antibody fragments such as single chain Fvs can be found in for example, Hudson P J & Kortt A A. "High avidity scFv multimers; diabodies and triabodies". J. Immunol. Meth. 231 (1999) 177-189; Adams G P & Schier R. "Generating improved single-chain Fv molecules for tumor targeting". J. Immunol. Meth. 231 (1999) 249-260; Raag R & Whitlow M. "Single-chain Fvs" FASEB J. 9 (1995) 73-80; Owens R J & Young R J. "The genetic engineering of monoclonal antibodies" J. Immunol. Meth. 168 (1994) 149-165.

Monoclonal antibodies directed against MAdCAM-1 are known in the art [10]. Two such antibodies, MECA-89 and MECA-367, are available from ATCC under accession nos. HB-292 and HB-9478 respectively.

Additional ligands that target MAdCAM-1 and vascular addressins may begenerated by using peptide display libraries such as those made in phage display technology (Burton D R. "Phage display. Immunotechnology." 1995 1:87-94; Cwirla S E, Peters E A, Barrett R W, Dower W J. Peptides on phage: a vast library of peptides for identifying ligands. Proc Natl Acad Sci U S A. 1990 87:6378-82; Scott J K, Smith G P. "Searching for peptide ligands with an epitope library." Science. 1990 249:386-90) as well as peptide libraries displayed on other surface components e.g. on flagella molecules (Westerlund-Wikstrom B. "Peptide display on bacterial flagella: principles and applications." Int J Med Microbiol. 2000 290:223-30) or on yeast (Boder E T, Wittrup K D. "Yeast surface display for screening combinatorial polypeptide libraries." Nat Biotechnol. 1997 15:553-7).

As will be recognised by those skilled in the field of protein chemistry there are numerous methods by which the antigen may be bound to the targeting moiety. Examples of such methods include:

1) affinity conjugation such as antigen-ligand fusions where the ligand has an affinity for the targeting antibody (examples of such ligands would be streptococcal protein G, staphylococcal protein A, peptostreptococcal protein L) or bispecific antibody to cross-link antigen to targeting moiety.

2) chemical cross-linking. There are a host of well known cross-linking methods including periodate-borohydride, carbodiimide, glutaraldehyde, photoaffinity labelling, oxirane and various succinimide esters such as maleimidobenzoyl-succinimide ester. Many of these are readily available commercially e.g. from Pierce, Rockford, Ill., USA. There are many references to cross-linking techniques including Hermanson G T "Bioconjugate Techniques" Academic Press, San Diego 1996; Lee Y C, Lee R T. Conjugation of glycopeptides to proteins. Methods Enzymol. 1989;179:253-7; Wong S S "Chemistry of Protein Conjugation and Cross-linking" CRC Press 1991; Harlow E & Lane D "Antibodies: A Laboratory Manual" Cold Spring Harbor Laboratory, 1988; Marriott G, Ottl J. Synthesis and applications of heterobifunctional photocleavable cross-lining reagents. Methods Enzymol. 1998;291:155-75.
3) genetic fusions. These can be made as recombinant antibody-antigen fusion proteins (in bacteria, yeast, insect or mammalian systems) or used for DNA immunization with or without spacers between the antibody and antigen. There are many publications of immunoglobulin fusions to other molecules. Fusions to antigens like influenza hamagglutinin are known in the art see, for example, Deliyannis G, Boyle J S, Brady J L, Brown L E, Lew A M. "A fusion DNA vaccine that targets antigen-presenting cells increases protection from viral challenge." Proc Natl Acad Sci U S A. 2000 97:6676-80. Short sequences can also be inserted into the immunoglobulin molecule itself [Lunde E, Western K H, Rasmussen I B, Sandlie I, Bogen B. "Efficient delivery of T cell epitopes to APC by use of MHC class II-specific Troybodies." J Immunol. 2002 168:2154-62]. Shortened versions of antibody molecules (e.g. Fv fragments) may also be used to make genetic fusions [Reiter Y, Pastan I. "Antibody engineering of recombinant Fv immunotoxins for improved targeting of cancer: disulfide-stabilized Fv immunotoxins." Clin Cancer Res. 1996 2:245-52].

As will be understood whatever the method of targeting moiety-antigen fusion used, such fusions need to be able to target the receptor, such as MAdCAM-1, in vivo. It is therefore highly preferred that the binding of the fusion to red blood cells or other cells (e.g. vascular endothelium of the lung) which it may encounter during its hematogenous traverse is minimal as such binding may inhibit the fusion reaching the desired sites within the GALT.

For similar reasons antigens which have a high propensity for binding to cells or tissues which the fusion may encounter on its route to the GALT should also be avoided.

Clearly the fusion process should be designed or selected so as not to interfere with the ability of the targeting moiety to bind to the receptor present in circulatory vessels in the GALT. This can be tested in vitro by determining whether the fusions bind the receptor, such as MAdCAM-1 on cryostat sections of the GALT by immunohistology or bind recombinant receptor proteins by ELISA.

The antigen used in the present invention can be any antigen against which it is desired to raise an immune response. It is preferred that the antigen is selected such that an immune response is generated against any pathogen whose main portal of entry is the gut and those that colonise mucosal surface. This would include *Salmonella, Cholera, Helicobacter pylori*, rectally introduced HIV, *Candida, P. gingivalis*, gut parasites or gut associated toxins. Moreover, the present invention may be used to induce an immune response to gut hormones (e.g. gastrin) or their receptors for gut associated cancers [Watson S A, Clarke P A, Morris T M, Caplin M E. "Antiserum raised against an epitope of the cholecystokinin B/gastrin receptor inhibits hepatic invasion of a human colon tumor." Cancer Res. 2000 60:5902-7; Smith A M, Justin T, Michaeli D, Watson S A. "Phase I/II study of G17-DT, an anti-gastrin immunogen, in advanced colorectal cancer." Clin Cancer Res. 2000 6:4719-24].

Information regarding HIV antigens such as gp120 and other candidates can be found in Stott J. Hu S L, Almond N. "Candidate vaccines protect macaques against primate immunodeficiency viruses." AIDS Res Hum Retroviruses. 1998 October;14 Suppl 3:S265-70.

Information regarding *Helicobacter pylori* antigens such as urease of *Helicobacter pylori* and other candidates can be found in Lee C K. "Vaccination against *Helicobacter pylori* in non-human primate models and humans." Scand J Immunol. 2001 May;53(5):437-42.

Further information regarding antigens in which mucosal immunity is important may be found in van Ginkel F W, Nguyen H H, McGhee J R. "Vaccines for mucosal immunity to combat emerging infectious diseases." Emerg Infect Dis. 2000 March-April;6(2):123-32; and Neutra M R, Pringault E, Kraehenbuhl J P. "Antigen sampling across epithelial barriers and induction of mucosal immune responses." Annu Rev Immunol. 1996;14:275-300.

As will be recognised the third to sixth aspects of the present invention relate to DNA vaccination.

The ability of direct injection of non-replicating plasmid DNA coding for viral proteins to elicit protective immune responses in laboratory and preclinical models has created increasing interest in DNA immunisation. A useful review of DNA vaccination is provided in Donnelly et al, Journal of Immunological Methods 176 (1994) 145-152, the disclosure of which is incorporated herein by reference.

DNA vaccination involves the direct in vivo introduction of DNA encoding an antigen into tissues of a subject for expression of the antigen by the cells of the subject's tissue. DNA vaccines are described in U.S. Pat. Nos. 5,939,400, 6,110,898, WO 95/20660 and WO 93/19183, the disclosures of which are hereby incorporated by reference in their entireties. The ability of directly injected DNA that encodes an antigen to elicit a protective immune response has been demonstrated in numerous experimental systems (see, for example, Conry et al., Cancer Res 54:1164-1168, 1994; Cardoso et al., Immuniz Virol 225:293-299, 1996; Cox et al., J Virol 67:5664-5667, 1993; Davis et al., Hum Mol Genet 2:1847-1851, 1993; Sedegah et al., Proc Natl Acad Sci USA 91:9866-9870, 1994; Montgomery et al., DNA Cell Biol 12:777-783, 1993; Ulmer et al., Science 259:1745-1749, 1993; Wang et al., Proc Natl Acad Sci USA 90:4156-4160, 1993; Xiang et al., Virology 199:132-140, 1994; Yang et al., Vaccine 15:888-891, 1997; Ulmer et al Science 259:1745, 1993; Wolff et al Biotechniques 11:474, 1991).

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression (Montgomery et al., DNA Cell Biol 12:777-783, 1993). High-velocity inoculation of plasmids, using a gene-gun, enhanced the immune responses of mice (Fynan et al., Proc Natl Acad Sci USA 90:11478-11482, 1993; Eisenbraun et al., DNA Cell Biol 12:791-797, 1993), presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

As used herein the term "animal" encompasses both human and non-human animals.

As used herein the term "circulatory vessel" encompasses both blood and lymphatic vessels.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in the specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will be described with reference to the following Examples.

The present inventors investigated whether targeting mucosal inductive sites such as the mesenteric lymph nodes (MLN) and Peyer's patches (PP) from the inside (via the blood) could be used to enhance the local mucosal immune response. The targeting strategy using the haematogenous rather than luminal route, bypasses the need for antigen to penetrate through the mucous membranes or survive the harsh conditions of the alimentary lumen. The present inventors used rat IgG2a antibodies MECA-367 & MECA-89 specific for the mucosal lymphocyte homing receptor MAdCAM-1 expressed in the high endothelial venules of the MLN and PP and in the flat epithelium of the lamina propria (LP) [8-10] as a model antigen. Antigen binding regions of these antibodies target them to this mucosal vascular addressin, eliciting responses that can be measured against the isotypic determinants of rat IgG2a (FIG. 1a). Immunization with anti-MAdCAM-1 antibody MECA-367 resulted in preferential localization of antigen to MLN and PP in-vivo (FIG. 1b), consistent with the predominant expression of MAdCAM-1 in mucosal tissues [8,10].

Methods

Immunizations

The three immunogens used were two rat IgG2a antibodies against mouse MAdCAM-1 (MECA-367 and MECA-89) and the control rat IgG2a (GL117 which recognizes E.coli-galactosidase). The immunogens were isolated from hybridoma culture supernatant and purified on protein G Sepharose (Amersham Pharmacia Biotech, Little Chalfont, UK) or purchased from PharMingen (San Diego, Calif., USA). 6-8 week old female CBA mice were used for all experiments.

Faecal Antibody Isolation

Mucosal antibody was isolated from faecal samples [18]. Briefly, 1 ml of 0.1 mg/ml soybean trypsin inhibitor (Sigma Chemical Co, St Louis, Mo., USA) in PBS was added per 0.1 g of faeces then vortexed in a mini-beadbeater (Biospec Products, Bartlesville, Okla., USA) for 10 sec at 2500 rpm, debris removed by centrifugation 9000 g, 4° C., for 15 min, and supernatant assayed for antibody.

Radioiodination

In-vivo antigen targeting was demonstrated by radiotracking 5 µCi iodinated protein (specific activity of 40 µCi/µg; total protein including cold protein=5 µg). Protein was radiolabeled with $I^{125}$ by the chloramine T method and injected intravenously. Organs harvested at 1 hour and radioactivity (cpm) for each whole tissue or 6 Peyer's patches determined on a gamma counter.

Immunological Assays

ELISA: Rat IgG2a specific antibody responses from serum, faecal and culture supernatant samples were determined by Enzyme-Linked Immunosorbent Assays (ELISA). Briefly, microtitre plates (Dynatech, Chantilly, Va., USA) coated with rat IgG2a (GL117, 2 µg/ml in PBS) were incubated with serially diluted sera, faecal extract, or culture supernatant in blocking buffer (5% skimmed-milk powder in PBS) overnight at 4° C. Bound antibody was detected after incubation with peroxidase-conjugated antibodies to mouse IgG (donkey anti-mouse, adsorbed against rat Ig, Chemicon, Temecula, Calif., USA), IgA (goat anti-mouse), IgG1, IgG2a, IgG2b, or IgG3 (rat anti-mouse) (Southern Biotechnology, Birmingham Ala., USA) diluted in blocking buffer. The substrate used was tetramethyl-benzidine (T2885, Sigma Chemical Co, St Louis, Mo., USA) in 0.1M sodium acetate pH 6 and reactions stopped with 0.5M sulphuric acid. IgG and IgA titres were defined as the reciprocal of the highest dilution to reach an $OD_{450nm}$ of 0.2 and 0.1 above background respectively.

ELISPOT: To determine the number of cell secreting antibody ELISPOT assay were performed. Briefly, 96 well sterile multiscreen filtration plates (Millipore S. A. Yvelines, Cedex, France) coated with rat IgG2a (GL117, 20 μg/ml in PBS) were incubated for 16 hrs at 37° C. 10% $CO_2$ with dilutions of single cell lymphocyte preparations isolated from mesenteric lymph nodes, Peyer's patches, spleen or lamina propria. Lamina propria lymphocytes were isolated as previously described [19]. Bound antibody was detected after incubation with peroxidase-conjugated antibodies to mouse IgA (Southern Biotechnology, Birmingham, Ala., USA) diluted in blocking buffer. Number of spots representing individual antigen specific ASC were counted under a stereo microscope after development with AEC substrate (Dako Co, Carpinteria, Calif., USA).

Gastrointestinal explant culture: Gastrointestinal explant cultures were performed using described methods [19,20]. Briefly, Peyer's patches were removed and the remaining small intestines were stripped of epithelium with 5 mM EDTA, washed and cut into 3 $mm^2$ pieces. 20 halved Peyer's patches pieces or 20 intestinal segments were cultured on gelfoam (Amersham Pharmacia Biotech, Little Chalfont, UK) in 2.5 ml of RPMI with 10% foetal calf serum at 37° C. 10% $CO_2$ for 6 days and culture supernatant used for analysis.

Cell culture and Cytokine production: Lymphocytes were cultured for 72 hours at $5 \times 10^6$ cells/ml in 2 ml in the presence of rat IgG2a (GL117, 40 g/ml). Cytokine levels in the supernatant were evaluated by sandwich ELISA. Recombinant cytokines as standards, coating antibody and biotinylated antibody were obtained from PharMingen (San Diego, Calif., USA).

Cloning: Antigen binding domains (variable regions) of the heavy and light chains of anti-MAdCAM-1 antibodies (MECA-367 and MECA-89) and isotype control antibody (GL117) were RT-PCRed from RNA isolated from the corresponding hybirdoma, using methods previously described Gilliland et al 1996 (Rapid and reliable cloning of antibody variable regions and generation of recombinant single chain antibody fragments. Tissue Antigens 47, 1-20). Variable domain of the light chains were cloned into an expression vector containing rat light chain constant region (Zhan, Y., Martin, R. M., Sutherland, R. M., Brady, J. L., and Lew, A. M. (2000). Local production of anti-CD4 antibody by transgenic allogeneic grafts affords partial protection, Transplantation 70, 947-54). Variable antigen binding domains of the heavy chains were cloned into expression vectors containing mouse IgG2c constant regions as previously described (Zhan, Y., Martin, R. M., Sutherland, R. M., Brady, J. L., and Lew, A. M. (2000). Local production of anti-CD4 antibody by transgenic allogeneic grafts affords partial protection, Transplantation 70, 947-54; Martin, R. M., Brady, J. L., and Lew, A. M. (1998). The need for IgG2c specific antiserum when isotyping antibodies from C57BL/6 and NOD mice, J Immunol Methods 212, 187-92. ) Antigens (OVA, *helicobacter* Urease B, *helicobacter* catalase, rotavirus VP7, *cholera* toxin B, mutant *cholera* toxin B) modified to contain Mlu-I/Xba-I cloning sites for antigen substitution, were fused to the CH3 domain of the Fc of mIgG2c heavy chain as previously described (Deliyannis, G., Boyle, J. S., Brady, J. L., Brown, L. E., and Lew, A. M. (2000). A fusion DNA vaccine that targets antigen-presenting cells increases protection from viral challenge, Proc Natl Acad Sci U S A 97, 6676-80.), using a 17 amino acid spacer.

The sequences of these constructs are set out in the Sequence Listing as follows:

| | |
|---|---|
| SEQ. ID. NO. 1 | GL117 light chain |
| SEQ. ID. NO. 2 | GL117-mIgG2c-ext-OVA |
| SEQ. ID. NO. 3 | MECA-367 light chain |
| SEQ. ID. NO. 4 | MECA-367-mIgG2c-ext-OVA |
| SEQ. ID. NO. 5 | MECA-89 light chain |
| SEQ. ID. NO. 6 | MECA-89-mIgG2c-ext-OVA |
| SEQ. ID. NO. 7 | Cholera toxin B |
| SEQ. ID. NO. 8 | double mutant (dm) Cholera toxin B |
| SEQ. ID. NO. 9 | *Helicobacter pylori* catalase |
| SEQ. ID. NO. 10 | *Helicobacter felis* urease B |
| SEQ. ID. NO. 11 | *Helicobacter pylori* urease B |
| SEQ. ID. NO. 12 | Rotavirus VP7 |

Heavy and light chain constructs from GL117 and MECA-367 were transfected into CHO cells using FuGENE (Roche, Mannheim, Germany) reagent according to manufacturers instructions. Supernatant was harvested 3 days after transfection and antibody binding to mouse MAdCAM-1 was tested on frozen sections of Peyer's patches and mesenteric lymph nodes by immunofluorescence. S/N from anti-MAdCAM-1 construct (MECA-367) but not from isotype control (GL117) showed binding to mucosal high endothelial venules. This demonstrated that anti-MAdCAM-1 antibody constructs (MECA-367) retain binding to mouse MAdCAM-1.

Results

Figure 2:
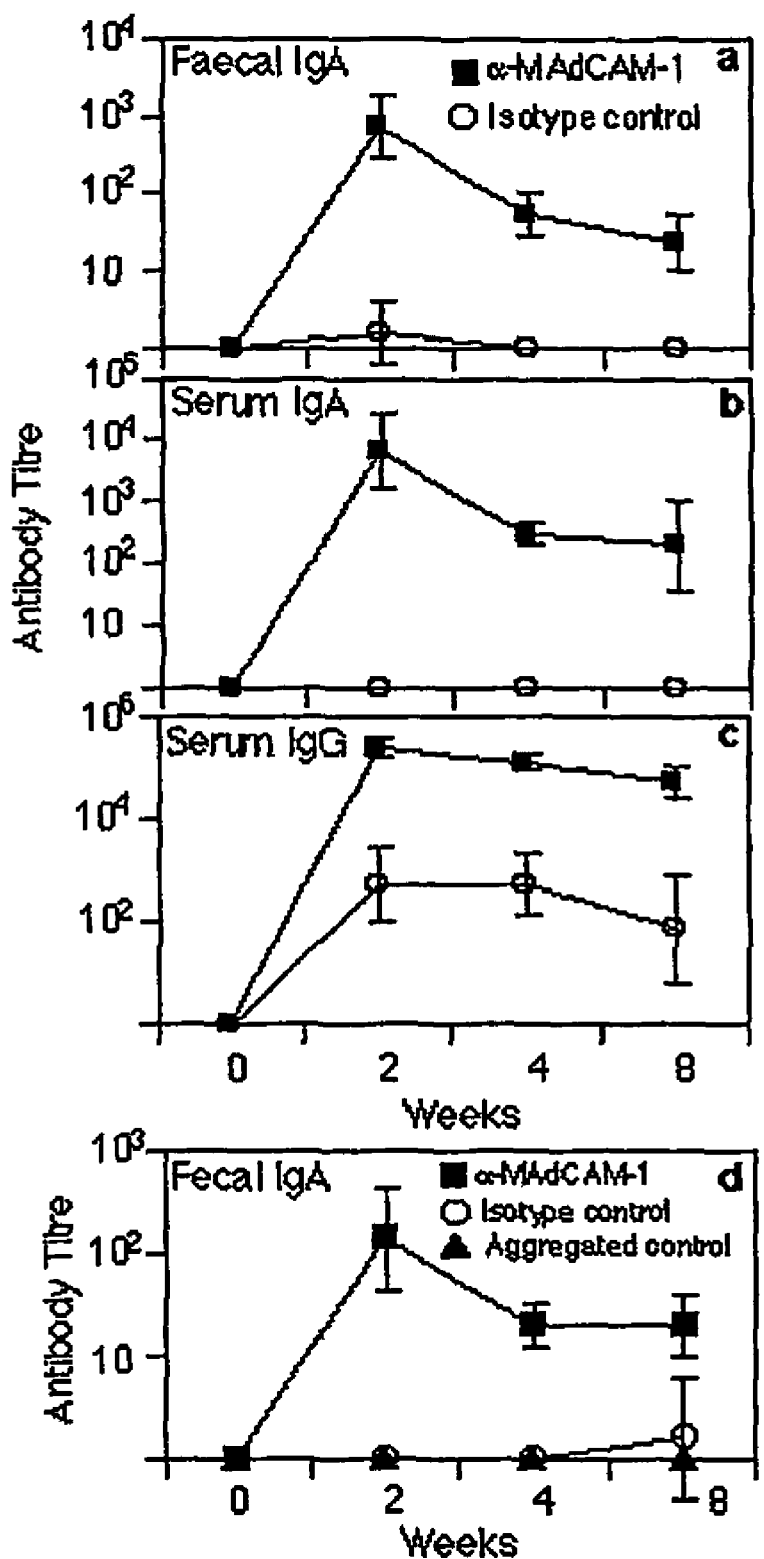
FIG. 2. MAdCAM-1 antigen targeting induces mucosal and augments systemic immune response. Mice (5 per group) were immunized intravenously with 100 g of either anti-MAdCAM-1 antibody MECA-367 or isotype control GL117 in saline. Rat IgG2a specific antibody responses for faecal IgA a, serum IgA b, and serum IgG c, were measured by ELISA at 2, 4, and 8 weeks; Mean and standard deviation of antibody titres ($\log_{10}$) are shown. Faecal IgA responses (representing mucosal responses) were detected only when the antigen was targeted to MAdCAM-1 a. Moreover, such targeting greatly augmented the systemic IgA and IgG response b & c. Proteins were either heat aggregated (70° C. 15 mins) or cleared of aggregates by ultacentrifugation ($5 \times 10^5$ g, 20 min) to investigate their effect on the mucosal antibody response d. Mice (5 per group) were immunized intravenously with 100 g of either aggregate free anti-MAdCAM-1 antibody MECA-89, aggregate free isotype control GL117, or heat aggregated isotype control GL117. Aggregation of protein had no effect on the mucosal antibody response. Moreover, targeting MAdCAM-1 with another rat IgG2a antibody MECA-89, resulted in similar enhancement in faecal antibody to that seen with MECA-367.

MAdCAM-1 antigen targeting elicits a mucosal response and augments systemic response (FIG. 2). As expected, mice immunized with non-targeted isotype control did not develop a faecal antibody response (FIG. 2a). In contrast, MAdCAM-1 antigen targeting induced an antigen specific faecal IgA antibody response that peaked at 2 weeks and remained detectable at 8 weeks (FIG. 2a). It should be noted that total faecal IgA immunoglobulin was not altered by targeting. In the systemic compartment, antibody responses were also augmented with MAdCAM-1 targeting. Following similar kinetics to the faecal antibody response, MAdCAM-1 antigen targeting induced a serum IgA antibody response whereas non-targeted isotype control immunization did not (FIG. 2b). The serum IgG antibody response with MAdCAM-1 targeting was enhanced 1000-fold above that without targeting (FIG. 2c). The serum IgG response was predominantly of the IgG1 isotype and could be further elevated, along with the mucosal antibody response, by intraperitoneal boosting with targeted or non-targeted antigen (data not shown). Similarly augmented responses were obtained through targeting of another anti-MAdCAM-1 antibody (MECA-89) that recognizes an epitope from a different extracellular domain of MAdCAM-1 [10] (FIG. 2d). As proteins may be more immunogenic when they are aggregated, we wanted to show that the enhanced effect of MECA antibodies was not due to an increased amount of aggregation within these samples. Mucosal IgA antibody elicited by MAdCAM-1 targeting was independent of protein aggregation as faecal IgA antibody responses could be detected after immunization with aggregate free anti-MAdCAM-1 antibody; moreover, heat aggregated isotype control did not induce faecal IgA antibody response (FIG. 2d). Likewise, serum IgG responses from aggregate free anti-MAdCAM-1 antibody remained 3 log higher than untreated isotype controls (data not shown).

Figure 3:
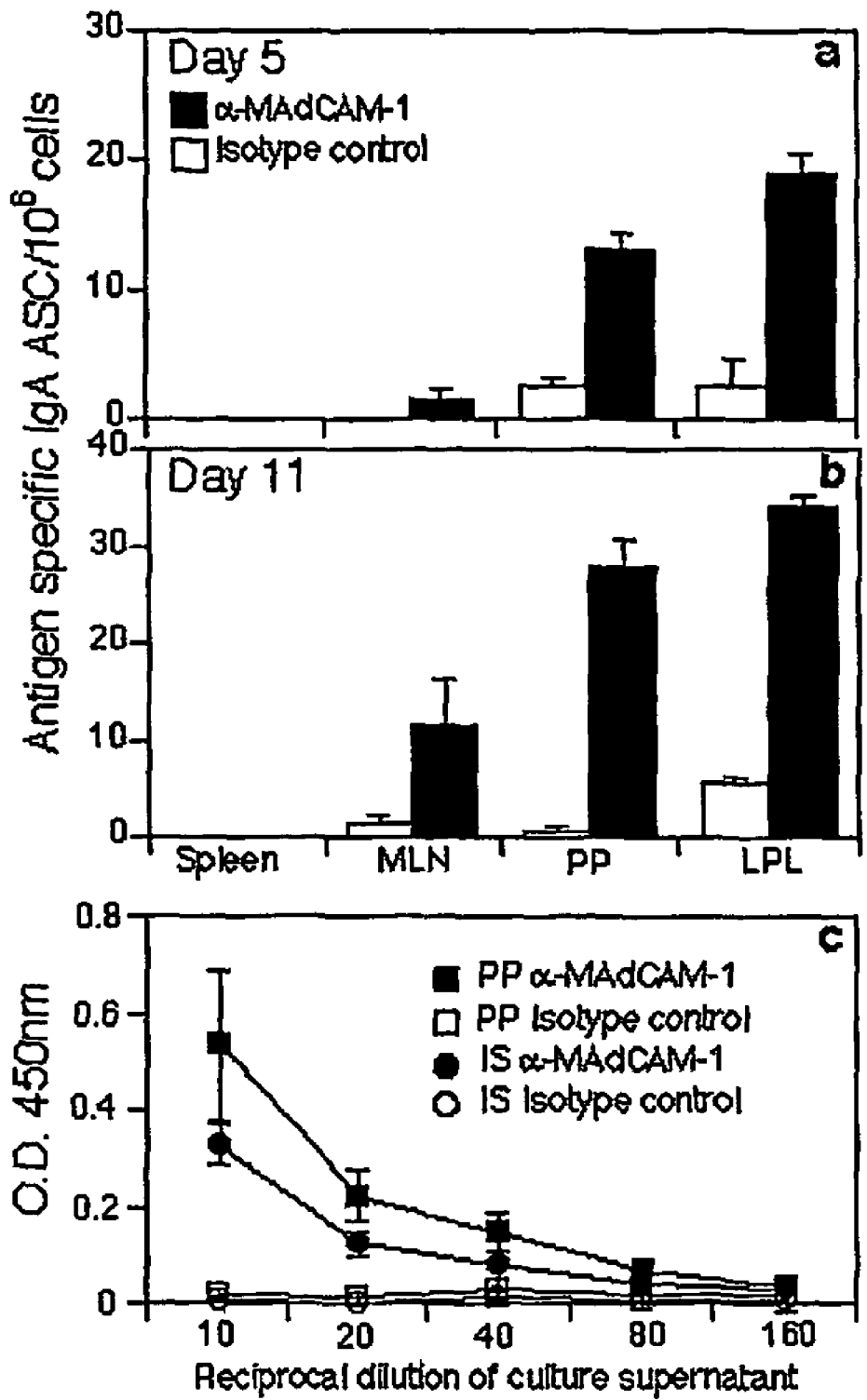
FIG. 3. Mucosal immune response elicited by MAdCAM-1 targeting is local. a & b, Mice (3 per group) were immunized intravenously with 100 g of either MECA-367 or the isotype control GL117. Five and 11 days after, mesenteric lymph node (MLN), Peyer's patches (PP) and lamina propria lymphocytes (LPL) were harvested and assayed for rat IgG2a specific IgA antibody secreting cells (ASC) by ELISPOT; Mean and standard deviation (spots/$10^6$) cell are shown. MAdCAM-1 targeted immunization induced antigen specific B-cell responses in MLN, PP and LPL. c, Antigen specific IgA is secreted by gastrointestinal explants after MAdCAM-1 targeting. Mice (3 per group) were immunized intravenously with 100 g of either MECA-367 or the isotype control GL117. Peyer's patches (PP) and intestinal segments (IS) were taken at 10 days and cultured in-vitro for 6 days. Antigen specific IgA in the culture supernatant was measured by ELISA; Mean and standard deviation of the optical density (O.D.) are shown. MAdCAM-1 targeted immunization induced a mucosal antibody response that could be detected in both PP and intestinal segment cultures.

Gut IgA is made locally in humans but can be translocated from the blood in rodents [11]. We therefore wanted to determine whether IgA antibody in the faecal samples was of local origin. A substantial increase in antigen specific IgA antibody secreting cells was found in MLN, PP, and LP lymphocyte preparations (FIG. 3a&b). IgA antibody secreting cells could be detected in the PP and LP as early as 5 days after primary immunization (FIG. 3a) indicating that B-cells were stimulated in these sites. The number of IgA antibody secreting cells increased at day 11 in all three important sites of the GALT (FIG. 3b). Antibody secreting cells were not detected in the spleen at 5 or 11 days after immunization (FIG. 3a&b) suggesting that the primary source of serum antibodies were derived from the GALT and not the spleen. For further confirmation of local GALT antibody production, supernatants from gastrointestinal explant cultures were tested for antibody by ELISA. Antigen specific IgA could be detected in culture supernatants of PP and intestinal segments from MAdCAM-1 targeted, but not from the non-targeted immunizations (FIG. 3c). Thus, MAdCAM-1 antigen targeting elicits local mucosal B-cell responses in the GALT.

Figure 4:
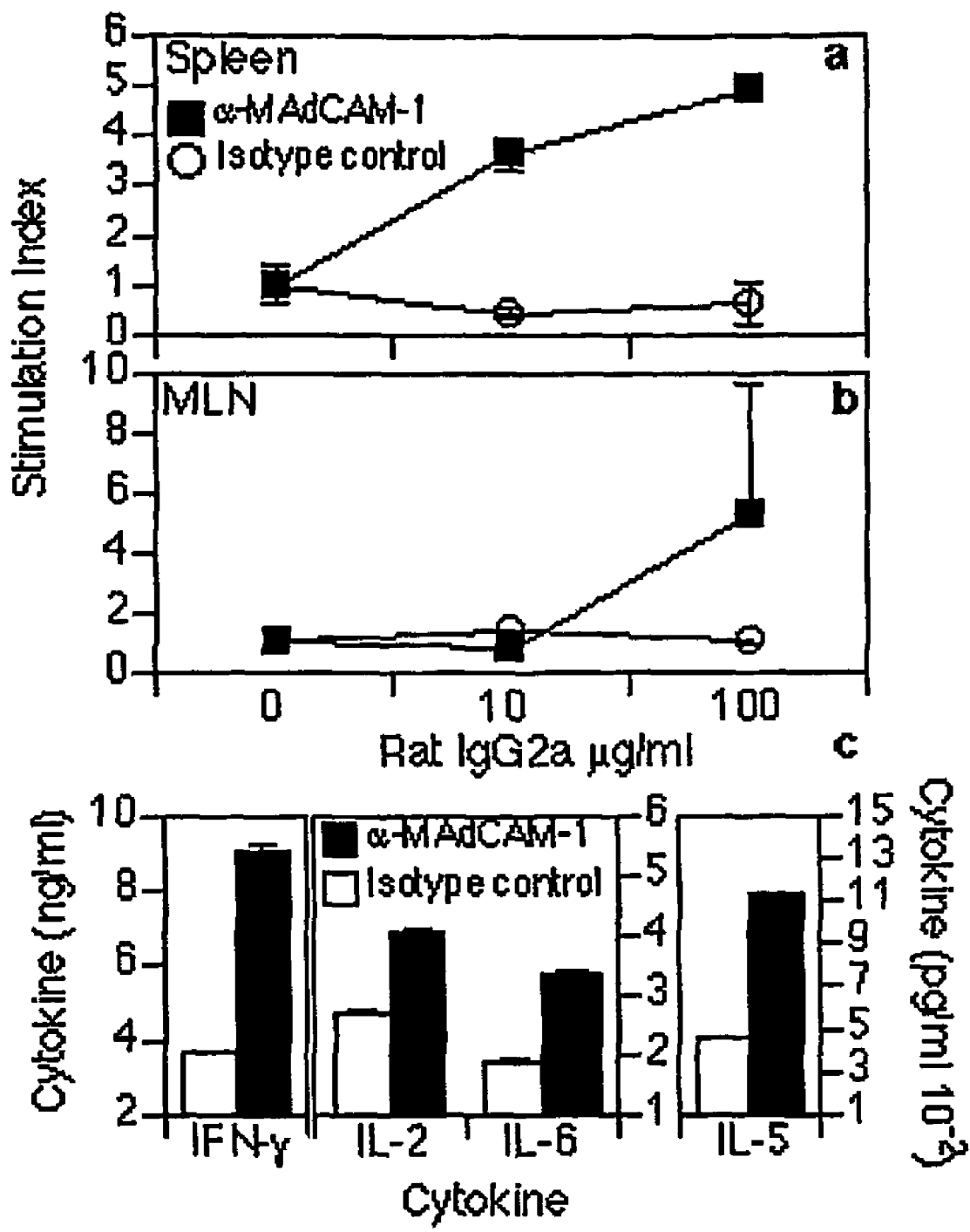
FIG. 4. MAdCAM-1 targeting enhances mucosal and systemic cytokine responses. Mice (3 per group) were immunized intravenously with 100 g of either MECA-367 or isotype control GL117 and boosted intraduodenally at 2 weeks. After 3 days, spleens and MLN cells were harvested and cultured for 72 hours in 40 g/ml GL117. Cytokines IL-2, and IFN-γ were measured in culture supernatant by ELISA; Mean and standard deviation of cytokine levels are shown. MAdCAM-1 targeted immunization resulted in enhanced levels of IL-2 and IFN-γ from both spleen and MLN cell cultures.
Figure 5:
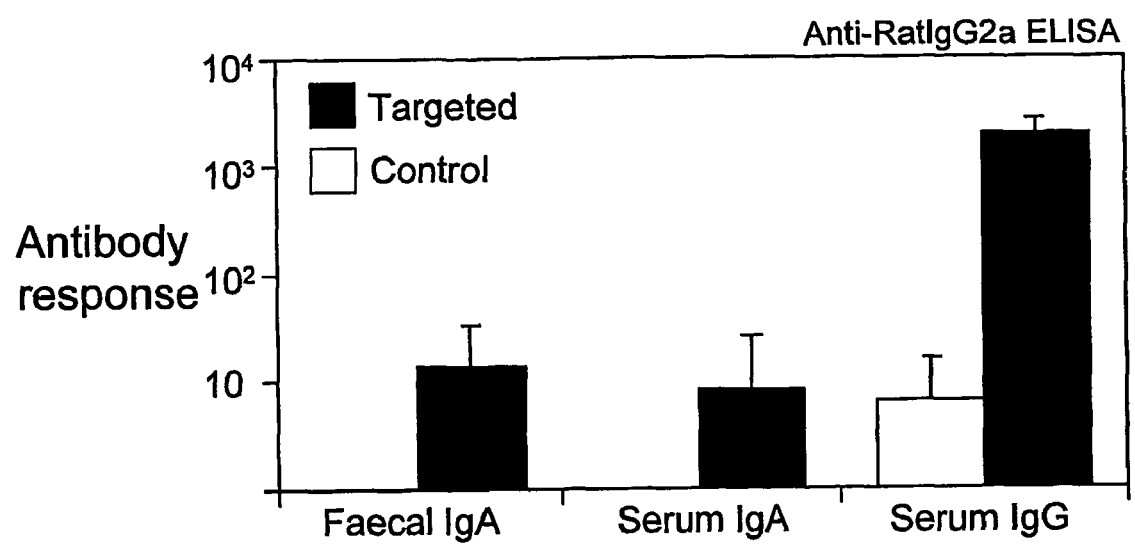
FIG. 5. Enhancement by MAdCAM-1 targeting is also effective by the intramuscular route. Mice (5 per group) were immunized intramuscularly with 100 g of either anti-MAdCAM-1 (MECA-367) or isotype control (GL117) in 0.2 ml of saline (0.1 ml into each quadriceps). Rat IgG2a specific antibody responses for faecal IgA, serum IgA and serum IgG were measured by ELISA at 2 weeks; Means±SD are shown.
Figure 6:
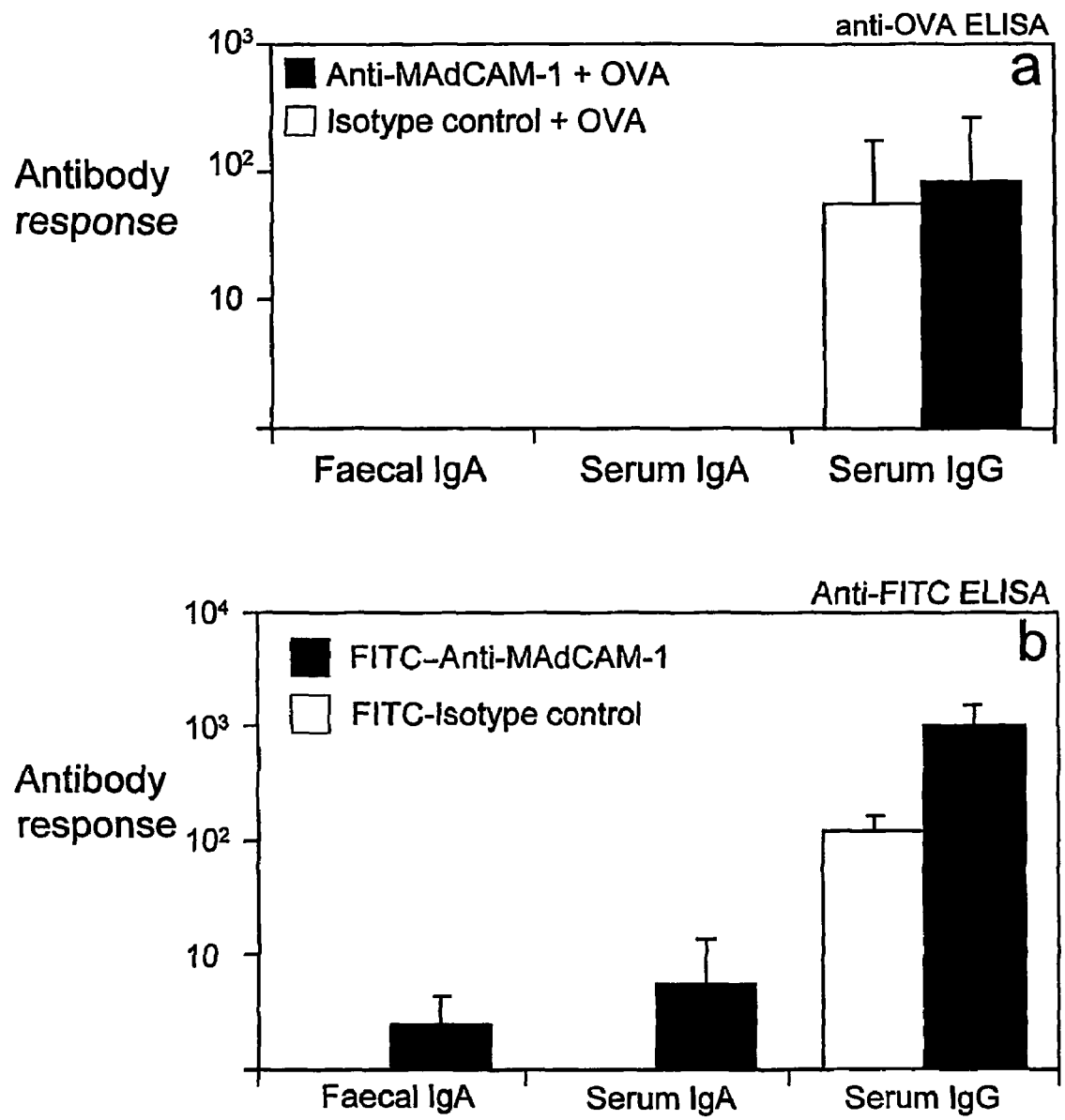
FIG. 6. Enhancement by MAdCAM-1 targeting is specific for the targeted antigen and can be shown for another antigen. (a) Mice (5 per group) were immunized intravenously with 100 g of either MECA-367 or isotype control GL117 plus 500 g of ovalbumin (OVA) in 0.3 ml of saline. OVA specific antibody responses for faecal IgA, serum IgA and serum IgG were measured by ELISA at 2 weeks. (b) Mice were immunized intravenously with 60 g of either Fluorescein isothiocyanate (FITC) conjugated anti-MAdCAM-1 antibody (MECA-89) or isotype control antibody (GL117) in 0.2 ml of saline. FITC specific antibody responses for faecal IgA, serum IgA and serum IgG were measured by ELISA at 2 weeks. Means±SD are shown.
Figure 7:
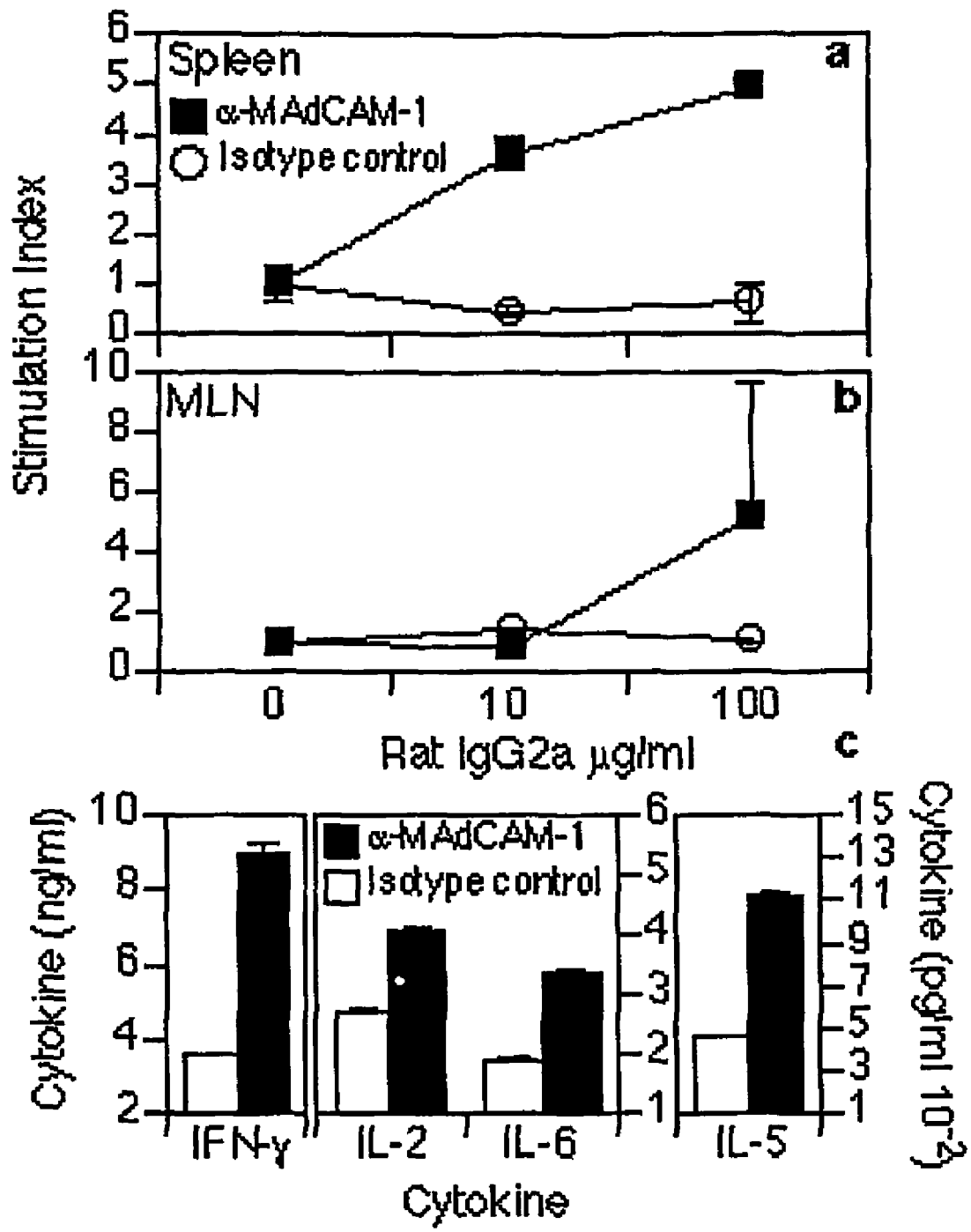
FIG. 7. MAdCAM-1 targeting enhances T-cell cytokine and proliferative responses. Mice were immunized intravenously with 1 g of either MECA-89 or isotype control GL117 in 0.1 ml of saline on days 0,2,4,7,9,12 and boosted intraperitoneally at day 18 with 100 g of GL117 in CFA. Ten days after, spleens and MLN cells were harvested. Antigen induced proliferation of splenic (a) and MLN (b) T-cells was determined in a standard 5 day 3H-thymidine uptake protocol. Mean stimulation index±SEM shown. (c) Antigen induced cytokine responses were evaluated by culturing splenocytes in the presence of rat IgG2a (GL117, 40 g/ml). Cytokine levels in the supernatant were measured by sandwich ELISA; Mean±SD shown.
Figure 8:
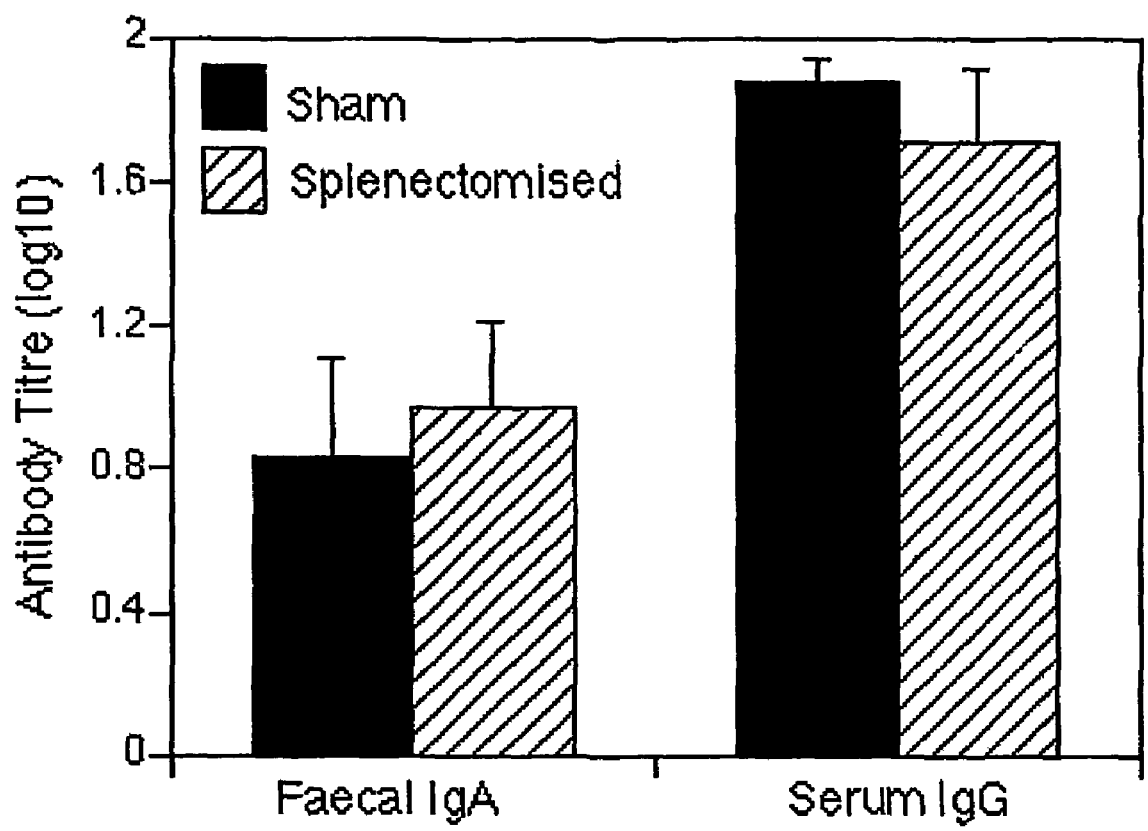
FIG. 8. Enhancement by MAdCAM-1 targeting is independent of splenic antigen localisation. Splenectomy or sham operations were performed on Mice (5 per group). One week after operation mice were immunized intravenously with 100 g of either anti-MAdCAM-1 (MECA-367) or isotype control (GL117) in 0.2 ml of saline. Rat IgG2a specific antibody responses for faecal IgA and serum IgG were measured by ELISA at 2 weeks; Means±SD of two independent experiments are shown.
Figure 9:
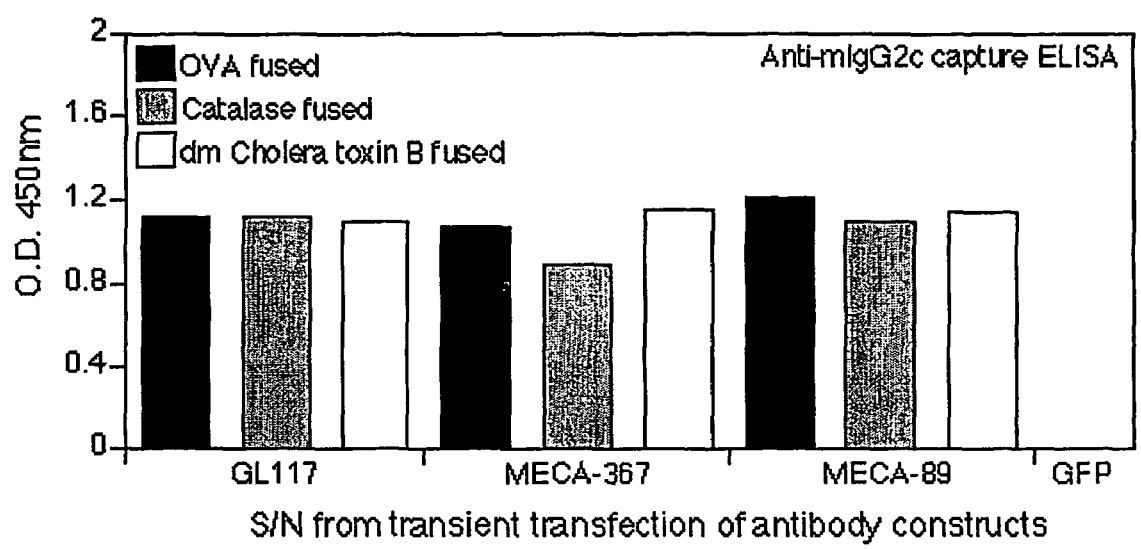
FIG. 9. IgG can be detected from transient transfection of antibody constructs. Heavy and light chain constructs from GL117, MECA-367 and MECA-89 were transfected into CHO cells using FuGENE (Roche, Mannheim, Germany) reagent according to manufacturers instructions. S/N was harvested 3 days after transfection and levels of mouse IgG2c was determined by capture ELISA. Mean O.D. 450 nm are shown.
Figure 10:
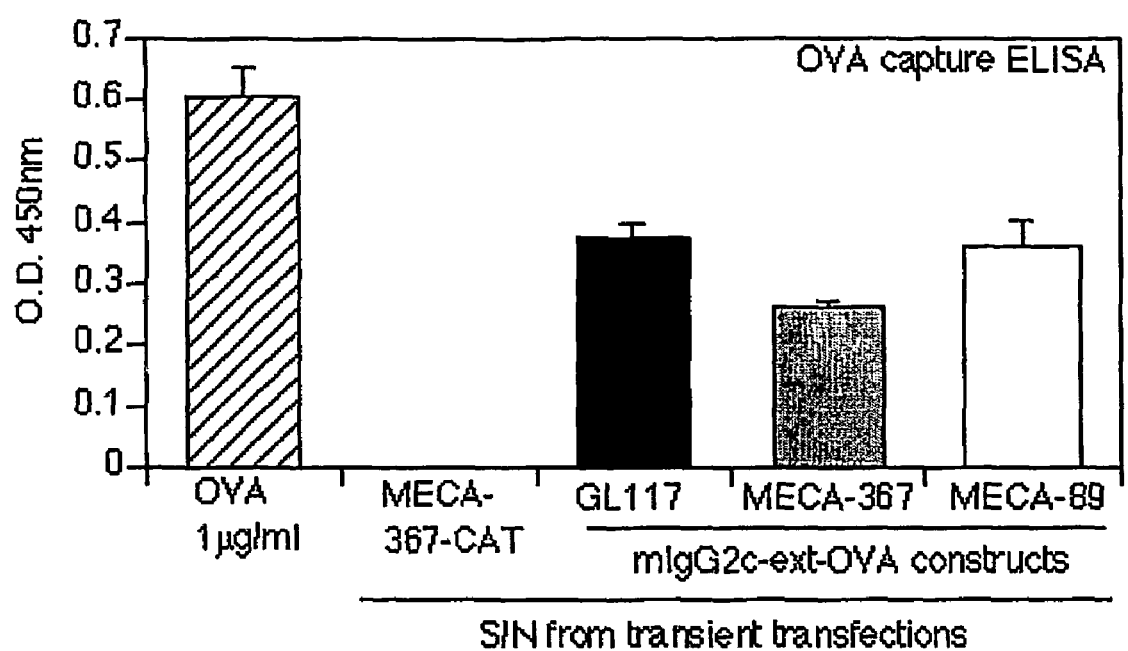
FIG. 10. Genetically fused antigen can be detected from transient transfection of antibody constructs. Heavy and light chain constructs from GL117, MECA-367 and MECA-89 were transfected into CHO cells using FuGENE (Roche, Mannheim, Germany) reagent according to manufacturers instructions. S/N was harvested 3 days after transfection and levels of ovalbumin (OVA) was determined by capture ELISA. Means±SD (O.D. 450 nm) are shown.
Figure 11:
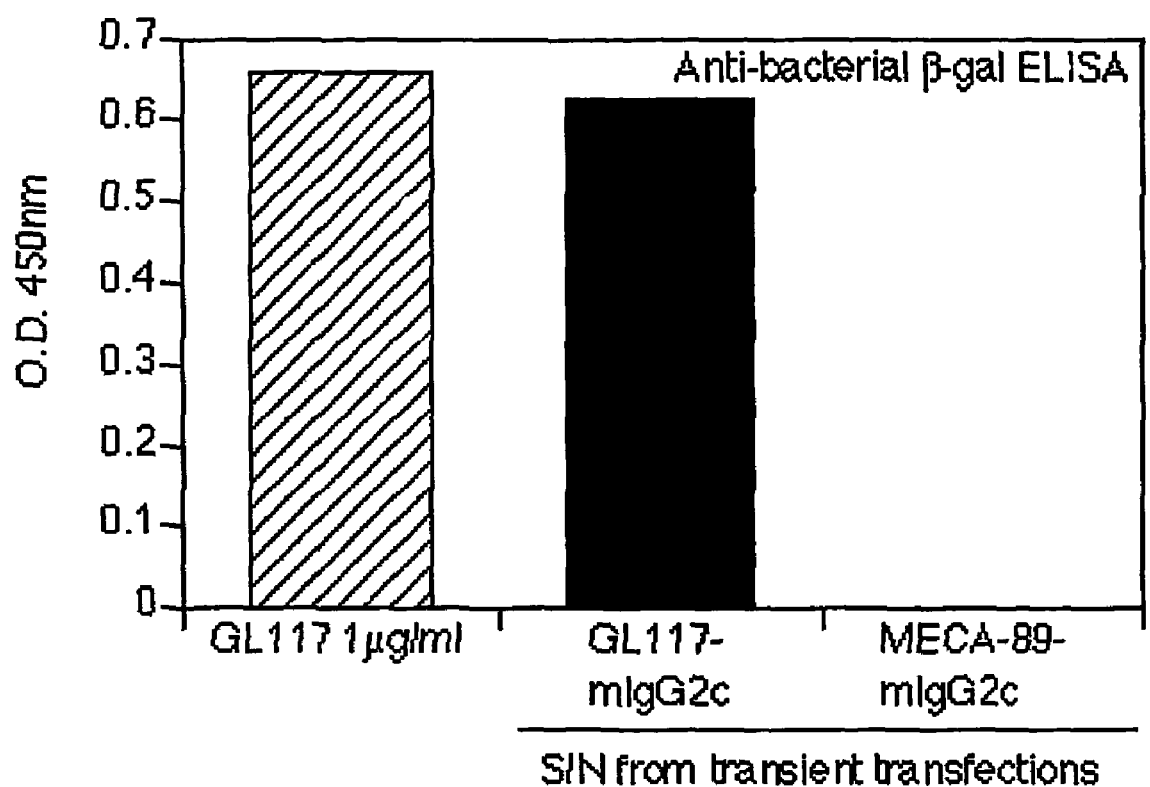
FIG. 11. Isotype control antibody (GL117) constructs retain binding to bacterial-galactosidase. Heavy and light chain constructs from GL117 and MECA-89 were transfected into CHO cells using FuGENE (Roche, Mannheim, Germany) reagent according to manufacturers instructions. S/N was harvested 3 days after transfection and antibody binding to bacterial-galactosidase determined by ELISA. Means±SD (O.D. 450 nm) are shown.

The presence of antigen specific IgA antibody secreting cells in the PP and LP only 5 days after immunization (FIG. 3a) suggests a strong role for the intestinal sites in the early induction of the mucosal antibody response to MAdCAM-1 targeted antigen. The concentration of antibody secreting cells in the MLN was unremarkable until day 11 (FIG. 3a&b). It is possible that B-cell responses detected in the MLN at day 11 resulted from B-cell stimulation at this site. However, we favour the proposal that they are derived from cells trafficking from the intestine to MLN, given the delay in the MLN response and the much higher concentration of specific B cells in the two intestinal sites. T-cell responses were also measured. Enhanced antigen specific secretion of IL-2 and IFN-γ could be detected from MAdCAM-1 targeted immunized mice (FIG. 4). As these were detected only after boosting it remains moot whether this represents direct T-cell activation at this site or the result of lymphocyte trafficking. Overall, these data indicate that augmented antigen specific antibody responses in both mucosal and systemic lymphoid compartments induced by MAdCAM-1 antigen targeting, is associated with an enhanced T-cell cytokine response (FIG. 4).

MAdCAM-1 expression is predominant in the GALT [9]. However, there is physiological expression at other sites. Follicular dendritic cells (FDC) expressing MAdCAM-1 [12] are found in secondary lymphoid organs and are important in antigen presentation and costimulation for B-cells and the maintenance of memory [13]. It was possible therefore, that augmented responses attained with MAdCAM-1 antigen targeting resulted from effective antigen localization to FDC. Adult mice also express MAdCAM-1 on the sinus lining cells of the spleen [14]. However, we could not detect any preferential localization of MAdCAM-1 targeted antigen in the spleen (FIG. 1b). This lack of preferential localization and the lack of antibody secreting cells in the spleen (FIG. 3a&b) would indicate that the localization to the spleen or FDC alone was not important for the augmented responses. We therefore argue that localization to the endothelia of the GALT is the key mechanism for the augmented responses. For the same reasons outlined above, it is likely that the enhancement of systemic antibody responses (FIG. 2b&c) resulted primarily from antigen targeting to the GALT and not the spleen. This is further supported by the fact that an increase in serum IgA parallels that of faecal IgA (FIG. 2a&b) and that systemic antibody can result from mucosal responses [6,15,16]. This is not surprising as the GALT comprises the majority of secondary lymphoid tissue in the body.

Localization of antigen to lymphoid sites is a powerful way of generating immune responses [1,7,17]. We found that antigen delivered to a mucosal vascular addressin in the lymphoid tissue of the gut using the blood route would elicit strong mucosal responses. The blood route avoids the need for antigen to penetrate through mucous membranes or survive the harsh conditions throughout the alimentary tract.

It will be appreciated by persons skilled in the art that numerous variations and/or modifications maybe made to the invention as shown in the specific embodiments without departing from the spirit or scope of the invention as broadly described. The present embodiments are, therefore, to be considered in all respects as illustrative and not restrictive.

REFERENCES

1. Czerkinsky, C. et al. Mucosal immunity and tolerance: relevance to vaccine development. *Immunol Rev* 170, 197-222. (1999).
2. Zinkernagel, R. M. et al. Antigen localisation regulates immune responses in a dose- and time-dependent fashion: a geographical view of immune reactivity. *Immunol Rev* 156, 199-209 (1997).
3. Ermak, T. H. & Giannasca, P. J. Micropartide targeting to M cells. *Adv Drug Deliv Rev* 34, 261-283 (1998).
4. Frey, A. & Neutra, M. R. Targeting of mucosal vaccines to Peyer's patch M cells. *Behring Inst Mitt*, 376-389 (1997).
5. Elson, C. O. & Ealding, W. Generalized systemic and mucosal immunity in mice after mucosal stimulation with cholera toxin. *J Immunol* 132, 2736-2741 (1984).
6. Kawabata, S., Terao, Y., Fujiwara, T., Nakagawa, I. & Hamada, S. Targeted salivary gland immunization with plasmid DNA elicits specific salivary immunoglobulin A and G antibodies and serum immunoglobulin G antibodies in mice. *Infect Immun* 67, 5863-5868 (1999).
7. Lehner, T. et al. Protective mucosal immunity elicited by targeted iliac lymph node immunization with a subunit SIV envelope and core vaccine in macaques. *Nat Med* 2, 767-775 (1996).
8. Briskin, M. J., McEvoy, L. M. & Butcher, E. C. MAdCAM-1 has homology to immunoglobulin and mucin-like adhesion receptors and to IgA1. *Nature* 363, 461-464 (1993).
9. Briskin, M. et al. Human mucosal addressin cell adhesion molecule-1 is preferentially expressed in intestinal tract and associated lymphoid tissue. *Am J Pathol* 151, 97-110 (1997).
10. Streeter, P. R., Berg, E. L., Rouse, B. T., Bargatze, R. F. & Butcher, E. C. A tissue-specific endothelial cell molecule involved in lymphocyte homing. *Nature* 331, 41-46 (1988).
11. Delacroix, D. L. et al. The liver in the IgA secretory immune system. Dogs, but not rats and rabbits, are suitable models for human studies. *Hepatology* 3, 980-988 (1983).
12. Szabo, M. C., Butcher, E. C. & McEvoy, L. M. Specialization of mucosal follicular dendritic cells revealed by mucosal addressin-cell adhesion molecule-1 display. *J Immunol* 158, 5584-5588 (1997).
13. Tew, J. G. et al. Follicular dendritic cells and presentation of antigen and costimulatory signals to B cells. *Immunol Rev* 156, 39-52 (1997).
14. Kraal, G., Schornagel, K., Streeter, P. R, Holzmann, B. & Butcher, E. C. Expression of the mucosal vascular addressin, MAdCAM-1, on sinus-lining cells in the spleen. *Am J Pathol* 147, 763-771 (1995).
15. Harokopakis, E., Childers, N. K, Michalek, S. M., Zhang, S. S. & Tomasi, M. Conjugation of cholera toxin or its B subunit to liposomes for targeted delivery of antigens. *J Immunol Methods* 185, 31-42 (1995).

16. Sato, Y. et al. Injection of plasmid DNA into the gastric mucosa induces mucosal and systemic immunity. *Cell Immunol* 199, 58-63 (2000).
17. Boyle, J. S., Brady, J. L. & Lew, A. M. Enhanced responses to a DNA vaccine encoding a fusion antigen that is directed to sites of immune induction. *Nature* 392, 408-411 (1998).
18. Bromander, A. K., Ekman, L., Kopf, M., Nedrud, J. G. & Lycke, N. Y. IL-6-deficient mice exhibit normal mucosal IgA responses to local immunizations and Helicobacter felis infection. *J Immunol* 156, 4290-4297 (1996).
19. Kramer, D. R & Cebra, J. J. Early appearance of "natural" mucosal IgA responses and germinal centers in suckling mice developing in the absence of maternal antibodies. *J. Immunol* 154, 2051-2062 (1995).
20. Losonsky, G. A., Fantry, G. T., Reymann, M. & Lim, Y. Validation of a gastrointestinal explant system for measurement of mucosal antibody production: *Clin Diagn Lab Immunol* 6, 803-807 (1999).

The invention claimed is:

1. A method of raising an immune response in an animal, comprising:
    administering to the animal by a haematogenous route a composition comprising a carrier and an antigen bound to a targeting moiety wherein the targeting moiety binds to Mucosal Addressin Cellular Adhesion Molecule-1 present in circulatory vessels in Gut Associated Lymphoid Tissue, wherein the targeting moiety is selected from the group consisting of an antibody, an antibody fragment and an antibody binding domain; and
    allowing the animal to generate an IgA immune response to the antigen.

2. The method according to claim 1 wherein the targeting moiety is an antibody selected from the group consisting of MECA-89 and MECA-367.

3. The method according to any one of claims 1 and 2 wherein the antigen is selected from the group consisting of *Salmonella, Cholera, Helicobacter pylori*, HIV, *Candida, P. gingivalis*, gut parasite, gut associated toxin, gut hormone, gut hormone receptor and gut associated cancer antigens.

4. The method according to any one of claims 1 and 2 wherein the antigen is bound to the targeting moiety by a type of binding selected from the group consisting of affinity conjugation, chemical cross-linking and genetic fusions.

5. A method of raising an immune response in an animal, the method comprising:
    administering to the animal by a haematogenous route a composition comprising a carrier and an antigen bound to an antibody selected from the group consisting of MECA-89 and MECA-367.

6. The method according to claim 5 wherein the antigen is selected from the group consisting of *Salmonella, Cholera, Helicobacter pylori*, HIV, *Candida, P. gingivalis*, gut parasite, gut associated toxin, gut hormone, gut hormone receptor and gut associated cancer antigens; and
    wherein the antigen is bound to the antibody by a type of binding chosen from affinity conjugation, chemical cross-linking and genetic fusions.

7. A method of raising an immune response in an animal, comprising:
    administering to the animal by a haematogenous route a composition comprising a carrier and a targeting moiety-antigen fusion wherein the targeting moiety-antigen fusion binds to Mucosal Addressin Cellular Adhesion Molecule-1 present in circulatory vessels in Gut Associated Lymphoid Tissue, wherein the targeting moiety is selected from a group consisting of an antibody, an antibody fragment and an antibody binding domain; and
    allowing the animal to generate an IgA immune response to the antigen.

8. The method according to claim 7 wherein the targeting moiety is an antibody selected from the group consisting of MECA-89 and MECA-367.

9. The method according to any one of claims 7 and 8 wherein the antigen is from a source selected from the group consisting of *Salmonella, Cholera, Helicobacter pylori*, HIV, *Candida, P. gingivalis*, gut parasite, gut associated toxin, gut hormone, gut hormone receptor and gut associated cancer antigens.

10. The method according to any one of claims 7 and 8 wherein the antigen is bound to the targeting moiety by a type of binding selected from the group consisting of affinity conjugation, chemical crosslinking and genetic fusions.

11. A method of raising an immune response in an animal, comprising:
   administering to the animal a composition comprising:
   a carrier; and
   a fusion comprised of (a) a targeting moiety, and (b) an antigen;
   wherein the antigen is selected from the group consisting of *Salmonella, Cholera, Helicobacter Pylori*, HIV, *Candida, P. gingivalis*, gut parasite, gut associated toxin, gut hormone , gut hormone receptor and gut associated cancer antigens;
   wherein the targeting moiety binds to Mucosal Addressin Cellular Adhesion Molecule-1 present in circulatory vessels in Gut Associated Lymphoid Tissue and wherein the targeting moiety is selected from the group consisting of an antibody, an antibody fragment, and an antibody binding domain; and
   allowing the animal to generate an IgA immune response to the antigen.

\* \* \* \* \*

SEQUENCE LISTING

<160> NUMBER OF SEQ ID NOS: 12

<210> SEQ ID NO 1
<211> LENGTH: 699
<212> TYPE: DNA
<213> ORGANISM: Rattus sp.

<400> SEQUENCE: 1

| | | | | | | |
|---|---|---|---|---|---|---|
| atggctccag | ttcaactttt | agggcttttg | ctgctctgcc | tcccagccat | gagatgtgac | 60 |
| atccagatga | cccagtctcc | ttcactcctg | tctgcatctg | tgggagacag | agtcactctc | 120 |
| aactgcaaag | caagtcagaa | tattaataag | aacttagact | ggtatcagca | aaagcttgga | 180 |
| gaagcgccaa | aagtcctgat | atattataca | gacaatttgc | aaacgggctt | ctcatcaagg | 240 |
| ttcagtggca | gtggatctgg | tacagattac | acactcacca | tcagcagcct | gcagcctgaa | 300 |
| gatgttgcca | catattactg | ctatcagtat | aacagtgggc | ccacgtttgg | acctgggacc | 360 |
| aagctggaac | tgaaacgggc | tgatgctgca | ccaactgtat | ctatcttccc | accatccacg | 420 |
| gaacagttag | caactggagg | tgcctcagtc | gtgtgcctca | tgaacaactt | ctatcccaga | 480 |
| gacatcagtg | tcaagtggaa | gattgatggc | actgaacgac | gagatggtgt | cctggacagt | 540 |
| gttactgatc | aggacagcaa | agacagcacg | tacagcatga | gcagcaccct | ctcgttgacc | 600 |
| aaggctgact | atgaaagtca | taacctctat | acctgtgagg | ttgttcataa | gacatcatcc | 660 |
| tcacccgtcg | tcaagagctt | caacaggaat | gagtgttag | | | 699 |

<210> SEQ ID NO 2
<211> LENGTH: 2333
<212> TYPE: DNA
<213> ORGANISM: Rattus sp.

<400> SEQUENCE: 2

| | | | | | | |
|---|---|---|---|---|---|---|
| atggctgtcc | tggtgctgtt | gctctgcctg | gtgacatttc | caagctgtgt | cctgtcccag | 60 |
| gtgcagctga | aagagtcagg | acctggtctg | gtgcagccct | cacagaccct | gtctctcacc | 120 |
| tgcactgtct | ctgggttctc | actaattagc | tatcatgtaa | cctgggttcg | ccagcctcct | 180 |
| ggaaagagtc | tggtgtggat | gggaacaata | tggactggtg | gaggtagaaa | ttataattcg | 240 |
| gctgaacaat | cccgactgag | catcagccgg | gacacctcca | agagccaagt | tttcttaaaa | 300 |
| atgaacagtc | tgcaacctga | agacacaggc | acttactact | gtgccagaca | tcgagggggg | 360 |
| tataactacg | gctttgatta | ctggggccaa | ggagtcatgg | tcacagtctc | ctcagctgaa | 420 |
| acaacagccc | catctgtcta | tccactggct | cctggaactg | ctctcaaaag | taactccatg | 480 |
| gtgactctgg | gatgcctggt | caagggctat | ttccctgagc | cagtcaccgt | gacctggaac | 540 |
| tctggagccc | tgtccagtgg | tgtgcacacc | ttcccagctc | tcctgcagtc | tggcctctac | 600 |
| accctcagca | gctcagtgac | tgtaacctcg | aacacctggc | ccagccagac | catcacctgc | 660 |
| aatgtggccc | acccggcaag | cagcaccaaa | gtggacaaga | aaattgagcc | cagagtgccc | 720 |

-continued

| | |
|---|---|
| ataacacaga acccctgtcc tccactcaaa gagtgtcccc catgcgcagc tccagacctc | 780 |
| ttgggtggac catccgtctt catcttccct ccaaagatca aggatgtact catgatctcc | 840 |
| ctgagcccca tggtcacatg tgtggtggtg gatgtgagcg aggatgaccc agacgtccag | 900 |
| atcagctggt ttgtgaacaa cgtggaagta cacacagctc agacacaaac ccatagagag | 960 |
| gattacaaca gtactctccg ggtggtcagt gccctcccca tccagcacca ggactggatg | 1020 |
| agtggcaagg agttcaaatg caaggtcaac aacagagccc tcccatcccc catcgagaaa | 1080 |
| accatctcaa acccagagg gccagtaaga gctccacagg tatatgtctt gcctccacca | 1140 |
| gcagaagaga tgactaagaa agagttcagt ctgacctgca tgatcacagg cttcttacct | 1200 |
| gccgaaattg ctgtggactg gaccagcaat gggcgtacag agcaaaacta caagaacacc | 1260 |
| gcaacagtcc tggactctga tggttcttac ttcatgtaca gcaagctcag agtacaaaag | 1320 |
| agcacttggg aaagaggaag tcttttcgcc tgctcagtgg tccacgaggt gctgcacaat | 1380 |
| caccttacga ctaagaccat ctcccggtct ctgggtccgg agctgcaact ggaggagagc | 1440 |
| tgtgcggagg cgcaggacgg ggagctcgac acgcgtgagc tcatcaattc ctgggtagaa | 1500 |
| agtcagacaa atgaattat cagaaatgtc cttcagccaa gctccgtgga ttctcaaact | 1560 |
| gcaatggttc tggttaatgc cattgtcttc aaaggactgt gggagaaagc atttaaggat | 1620 |
| gaagacacac aagcaatgcc tttcagagtg actgagcaag aaagcaaacc tgtgcagatg | 1680 |
| atgtaccaga ttggtttatt tagagtggca tcaatggctt ctgagaaaat gaagatcctg | 1740 |
| gagcttccat ttgccagtgg gacaatgagc atgttggtgc tgttgcctga tgaagtctca | 1800 |
| ggccttgagc agcttgagag tataatcaac tttgaaaaac tgactgaatg gaccagttct | 1860 |
| aatgttatgg aagagaggaa gatcaaagtg tacttacctc gcatgaagat ggaggaaaaa | 1920 |
| tacaacctca catctgtctt aatggctatg gcattactg acgtgtttag ctcttcagcc | 1980 |
| aatctgtctg gcatctcctc agcagagagc ctgaagatat ctcaagctgt ccatgcagca | 2040 |
| catgcagaaa tcaatgaagc aggcagagag gtggtagggt cagcagaggc tggagtggat | 2100 |
| gctgcaagcg tctctgaaga atttagggct gaccatccat tcctcttctg tatcaagcac | 2160 |
| atcgcaacca acgccgttct cttctttggc agatgtgttt ccccttaaaa agaagaaagc | 2220 |
| tgaaaaactc tgtcccttcc aacaagaccc agagcactgt agtatcaggg gtaaaatgaa | 2280 |
| aagtatgtta tctgctgcat ccagacttca taaaagctgg agcttaatct aga | 2333 |

<210> SEQ ID NO 3
<211> LENGTH: 699
<212> TYPE: DNA
<213> ORGANISM: Rattus sp.

<400> SEQUENCE: 3

| | |
|---|---|
| atggctccag ttcaactttt agggcttttg ctgctctgcc tcccagccat gagatgtgac | 60 |
| atccagatga cccagtctcc ttcagtcctg tctgcatctg tgggagacag agtcactctc | 120 |
| agctgcaaaa caagtcagaa tactaataag aacttagact ggtatcagca aaagcttgga | 180 |
| gaagctccca actcctgat atattttaca acaatttgc aaacgggcat cccatcaagg | 240 |
| ttcagtggca gtggatctgg tacagattac acactcacca tcagcagcct gcagcctgaa | 300 |
| gatgttgcca catattactg ctatcagtat aacagtgggc cacgtttgg agctgggacc | 360 |
| aaactggaat tgagtcgggc tgatgctgca ccaactgtat ccatcttccc accatccatg | 420 |
| gaacagttaa catctggagg tgccacagtc gtgtgcttcg tgaacgactt ctatcccaga | 480 |
| gacatcagtg tcaagtggaa gattgatggc actgaacgac gagatggtgt cctggacagt | 540 |

```
gttactgatc aggacagcaa agacagcacg tacagcatga gcagcaccct ctcgttgacc      600
aaggctgact atgaaagtca taacctctat acctgtgagg ttgttcataa gacatcatcc      660
tcacccgtcg tcaagagctt caacaggaat gagtgttag                             699
```

<210> SEQ ID NO 4
<211> LENGTH: 2348
<212> TYPE: DNA
<213> ORGANISM: Rattus sp.

<400> SEQUENCE: 4

```
atggctgtcc tggtgctgtt gctctgcctg gtgacatttc caagctgtgc cctgtcccag       60
gtgcagctga aggagtcagg acctggtctg gtgcggccct cacagaccct gtccctcacc      120
tgcactgtct ctgggttctc aataaccagt aacggtgtaa gctgggttcg ccagcctccg      180
ggaaagggtc tggagtggat gggagcaata tggagtggtg aagtagaga ttataattca       240 gctctcaaat cccgattgag catcagcagg gacacctcca agagccaagt tttcttaaac      300
ttgaacagtc tgcaaactga agacacagcc atttacttct gtaccagatc ggattatcat      360
gatggtacct ccctatatta ctatgttatg gatgcctggg gtcaaggagc ttcagtcact      420
gtctcctcag ctgaaacaac agccccatct gtctatccac tggctcctgg aactgctctc      480
aaaagtaact ccatggtgac cctgggatgc ctggtcaagg ctatttccc tgagccagtc       540 accgtgacct ggaactctgg agccctgtcc agtggtgtgc acaccttccc agctctcctg      600
cagtctggcc tctacaccct cagcagctca gtgactgtaa cctcgaacac ctggcccagc      660
cagaccatca cctgcaatgt ggcccacccg gcaagcagca ccaaagtgga caagaaaatt      720
gagcccagag tgcccataac acagaacccc tgtcctccac tcaaagagtg tccccatgc       780 gcagctccag acctcttggg tggaccatcc gtcttcatct tccctccaaa gatcaaggat      840
gtactcatga tctcccctgag ccccatggtc acatgtgtgg tggtggatgt gagcgaggat      900
gacccagacg tccagatcag ctggtttgtg aacaacgtgg aagtacacac agctcagaca      960
caaacccata gagaggatta caacagtact ctccgggtgg tcagtgccct ccccatccag     1020
caccaggact ggatgagtgg caaggagttc aaatgcaagg tcaacaacag agccctccca     1080
tcccccatcg agaaaaccat ctcaaaaccc agagggccag taagagctcc acaggtatat     1140
gtcttgcctc caccagcaga agagatgact aagaaagagt tcagtctgac ctgcatgatc     1200
acaggcttct acctgccgga aattgctgtg gactggacca gcaatgggcg tacagagcaa     1260
aactacaaga caccgcaac agtcctggac tctgatggtt cttacttcat gtacagcaag     1320
ctcagagtac aaaagagcac ttgggaaaga ggaagtcttt tcgcctgctc agtggtccac     1380
gaggtgctgc acaatcacct tacgactaag accatctccc ggtctctggg tccggagctg     1440
caactggagg agagctgtgc ggaggcgcag gacggggagc tcgacacgcg tgagctcatc     1500
aattcctggg tagaaagtca gacaaatgga attatcagaa atgtccttca gccaagctcc     1560
gtggattctc aaactgcaat ggttctggtt aatgccattg tcttcaaagg actgtgggag     1620
aaaagcattt aaggatgaaga cacacaagca atgcctttca gagtgactga gcaagaaagc     1680
aaacctgtgc agatgatgta ccagattggt ttatttagag tggcatcaat ggcttctgag     1740
aaaatgaaga tcctggagct tccatttgcc agtgggacaa tgagcatgtt ggtgctgttg     1800
cctgatgaag tctcaggcct tgagcagctt gagagtataa tcaactttga aaaactgact     1860
gaatggacca gttctaatgt tatggaagag aggaagatca aagtgtactt acctcgcatg     1920
aagatggagg aaaaatacaa cctcacatct gtcttaatgg ctatgggcat tactgacgtg     1980
```

```
tttagctctt cagccaatct gtctggcatc tcctcagcag agagcctgaa gatatctcaa    2040
gctgtccatg cagcacatgc agaaatcaat gaagcaggca gagaggtggt agggtcagca    2100
gaggctggag tggatgctgc aagcgtctct gaagaattta gggctgacca tccattcctc    2160
ttctgtatca agcacatcgc aaccaacgcc gttctcttct ttggcagatg tgtttcccct    2220
taaaaagaag aaagctgaaa aactctgtcc cttccaacaa gacccagagc actgtagtat    2280
caggggtaaa atgaaaagta tgttatctgc tgcatccaga cttcataaaa gctggagctt    2340
aatctaga                                                              2348

<210> SEQ ID NO 5
<211> LENGTH: 699
<212> TYPE: DNA
<213> ORGANISM: Rattus sp.

<400> SEQUENCE: 5
atggctccag ttcaactctt agggctgctg ctgctctggc tcccagccat gagatgtgac      60
atccagatga cccagtctcc ttcattcctg tctgcatctg tgggagacag agtcactatc     120
aactgcaaag caagtcagaa tattaacaag tacttagact ggtatcagca aaagcttggt     180
gaagctccca aactcctgat atataatcca acagtttgc aaacaggaat cccatcaagg      240
ttcagtggca gtggatctgg tactgatttc acacttacca tcagcagcct gcagcctgaa     300
gatgtagcca catatttctg cctttcagcat aacagtgggt ggacgttcgg tggaggcacc    360
aagctggagt tgaaacgggc tgatgctgca ccaactgtat ctatcttccc accatccacg     420
gaacagttag caactggagg tgcctcagtc gtgtgcctca tgaacaactt ctatcccaga     480
gacatcagtg tcaagtggaa gattgatggc actgaacgac agagatggtgt cctggacagt    540 gttactgatc aggacagcaa agacagcacg tacagcatga gcagcaccct ctcgttgacc    600
aaggctgact atgaaagtca taacctctat acctgtgagg ttgttcataa gacatcatcc    660
tcacccgtcg tcaagagctt caacaggaat gagtgttag                            699

<210> SEQ ID NO 6
<211> LENGTH: 2342
<212> TYPE: DNA
<213> ORGANISM: Rattus sp.

<400> SEQUENCE: 6
atggattggg tgtggaactt gctatttctg atggcagttg cccaaacagg tgcccaagca      60
cagatccagt tggtacagtc tggacctgaa ctgaagaagc ctggagagtc agtgaagatc     120
tcctgcaagg cttctgggta taccttcaca gaccatgcaa tgcactgggt gaaacaggct     180
ccaggaaagg gcttgaagtg gatgggctgg atcaacacct atactgggaa gccaacatat     240
ggtgatgact ccaaggacg gtttgtcctc tctttggaag cctctgccag cactgcaaat     300
ttgcagatca gcaacctcaa aaatgaggac acggctacat atttctgtgc aagatcttat    360
ttctatgatt cctactggta ctttgacttc tggggcccag gaaccatggt caccgtgtcc    420
tcagctgaaa caacagcccc atctgtctat ccactggctc ctggaactgc tctcaaaagt    480
aactccatgg tgactctggg atgcctggtc aagggctatt ccctgagcc agtcaccgtg    540 acctggaact ctggagccct gtccagtggt gtgcacacct tccagctctc ctgcagtct     600 ggcctctaca ccctcagcag ctcagtgact gtaacctcga acacctggcc cagccagacc    660
atcacctgca atgtggccca ccggcaagc agcaccaaaa tggacaagaa aattgagccc    720
agagtgccca taacacagaa cccctgtcct ccactcaaag agtgtccccc atgcgcagct    780
```

```
ccagacctct tgggtggacc atccgtcttc atcttccctc caaagatcaa ggatgtactc      840
atgatctccc tgagccccat ggtcacatgt gtggtggtgg atgtgagcga ggatgaccca      900
gacgtccaga tcagctggtt tgtgaacaac gtggaagtac acacagctca gacacaaacc      960
catagagagg attacaacag tactctccgg gtggtcagtg ccctccccat ccagcaccag     1020
gactggatga gtggcaagga gttcaaatgc aaggtcaaca acagagccct cccatccccc     1080
atcgagaaaa ccatctcaaa acccagaggg ccagtaagag ctccacaggt atatgtcttg     1140
cctccaccag cagaagagat gactaagaaa gagttcagtc tgacctgcat gatcacaggc     1200
ttcttacctg ccgaaattgc tgtggactgg accagcaatg ggcgtacaga gcaaaactac     1260
aagaacaccg caacagtcct ggactctgat ggttcttact tcatgtacag caagctcaga     1320
gtacaaaaga gcacttggga agaggaagt cttttcgcct gctcagtggt ccacgaggtg      1380
ctgcacaatc accttacgac taagaccatc tcccggtctc tgggtccgga gctgcaactg     1440
gaggagagct gtgcggaggc gcaggacggg gagctcgaca cgcgtgagct catcaattcc     1500
tgggtagaaa gtcagacaaa tggaattatc agaaatgtcc ttcagccaag ctccgtggat     1560
tctcaaactg caatggttct ggttaatgcc attgtcttca aaggactgtg ggagaaagca     1620
tttaaggatg aagacacaca agcaatgcct ttcagagtga ctgagcaaga aagcaaacct     1680
gtgcagatga tgtaccagat tggtttattt agagtggcat caatggcttc tgagaaaatg     1740
aagatcctgg agcttccatt tgccagtggg acaatgagca tgttggtgct gttgcctgat     1800
gaagtctcag gccttgagca gcttgagagt ataatcaact ttgaaaaact gactgaatgg     1860
accagttcta atgttatgga agagaggaag atcaaagtgt acttacctcg catgaagatg     1920
gaggaaaaat acaacctcac atctgtctta atggctatgg gcattactga cgtgtttagc     1980
tcttcagcca atctgtctgg catctcctca gcagagagcc tgaagatatc tcaagctgtc     2040
catgcagcac atgcagaaat caatgaagca ggcagagagg tggtagggtc agcagaggct     2100
ggagtggatg ctgcaagcgt ctctgaagaa tttagggctg accatccatt cctcttctgt     2160
atcaagcaca tcgcaaccaa cgccgttctc ttctttggca gatgtgtttc cccttaaaaa     2220
gaagaaagct gaaaaactct gtcccttcca acaagaccca gagcactgta gtatcagggg     2280
taaaatgaaa agtatgttat ctgctgcatc cagacttcat aaaagctgga gcttaatcta     2340
ga                                                                    2342

<210> SEQ ID NO 7
<211> LENGTH: 324
<212> TYPE: DNA
<213> ORGANISM: Vibrio cholerae

<400> SEQUENCE: 7
acgcgtaccc cgcagaatat tactgatttg tgtgcagaat accacaacac acaaatacat       60
acgctaaatg ataagatatt ttcgtataca gaatctctag ctggaaaaag agagatggct      120
atcattactt ttaagaatgg tgcaactttt caagtagaag taccaggtag tcaacatata      180
gattcacaaa aaaagcgat tgaaaggatg aaggataccc tgaggattgc atatcttact      240
gaagctaaag tcgaaaagtt atgtgtatgg aataataaaa cgcctcatgc gattgccgca      300
attagtatgg caaattaatc taga                                             324

<210> SEQ ID NO 8
<211> LENGTH: 324
<212> TYPE: DNA
<213> ORGANISM: Vibrio cholerae
```

<400> SEQUENCE: 8

```
acgcgtaccc cgcagaatat tactgatttg tgtgcagaat accacaacac acaaatacat      60
acgctaaatg ataagatatt ttcgtataca gaatctctag ctgagaaaag agagatggct     120
atcattactt ttaagaatgg tgcaactttt caagtagaag taccaggtag tcaacatata     180
gattcacaaa aaaagtgat tgaaaggatg aaggataccc tgaggattgc atatcttact      240
gaagctaaag tcgaaaagtt atgtgtatgg aataataaaa cgcctcatgc gattgccgca     300
attagtatgg caaattaatc taga                                            324
```

<210> SEQ ID NO 9
<211> LENGTH: 417
<212> TYPE: DNA
<213> ORGANISM: Helicobacter pylori

<400> SEQUENCE: 9

```
acgcgtatgc aaaacgggta ttacggctct ttacaaaact atacgcctag ctcattgcct      60
ggctataaag aagataagag tgcaagggat cctaagttca acttagctca tattgagaaa     120
gagtttgaag tgtggaattg ggattacaga gctgaggata gcgattacta cacccaacca     180
ggtgattact accgctcatt gccagctgat gaaaagaaa ggttgcatga cactattgga      240
gagtctttag ctcatgttac cataaggaa attgtggata aacaattgga gcatttcaag      300
aaagctgacc ccaaatacgc tgagggagtt aaaaaagctc ttgaaaaaca ccaaaaaatg     360
atgaaagaca tgcatggaaa agacatgcac cacacgaaaa agaaaaagta atctaga         417
```

<210> SEQ ID NO 10
<211> LENGTH: 1719
<212> TYPE: DNA
<213> ORGANISM: Helicobacter felis

<400> SEQUENCE: 10

```
cgcgccccat gaaaaagatt tcacgaaaag aatatgtttc tatgtatggt cccactaccg      60
gggatcgtgt tagactcggc gacactgatt tgatcttaga agtggagcat gattgcacca     120
cttatggtga agagatcaaa tttggggcg gtaaaactat ccgtgatggg atgagtcaaa      180
ccaatagccc tagctcttat gaattagatt tggtgctcac taacgccctc attgtggact     240
atacgggcat ttacaaagcc gacattggga ttaaagacgg caagattgca ggcattggca     300
aggcaggcaa taaggacatg caagatggcg tagataataa tctttgcgta ggtcctgcta     360
cagaggcttt ggcagctgag ggcttgattg taaccgctgg tggcatcgat acgcatattc     420
actttatctc tccccaacaa atccctactg cttttgccag cggggttaca accatgattg     480
gaggaggcac aggacctgcg gatggcacga atgcgaccac catcactccc ggacgcgcta     540
atctaaaaag tatgttgcgt gcagccgaag aatacgccat gaatctaggc tttttggcta     600
aggggaatgt gtcttacgaa ccctctttac gcgatcagat tgaagcaggg gcgattggtt     660
ttaaaatcca cgaagactgg ggaagcacac ctgcagctat tcaccactgc ctcaatgtcg     720
ccgatgaata cgatgtgcaa gtggctatcc acaccgatac ccttaacgag gcgggctgtg     780
tagaagacac cctagaggcg attgccgggc gcaccatcca taccttccac actgaagggg     840
ctgggggtgg acacgctcca gatgttatca aaatggcagg gaattaac attctacccg       900
cctctactaa cccgaccatt cctttcacca aaaacactga agccgagcac atggacatgt     960
taatggtgtg ccaccacttg gataaaagta tcaaggaaga tgtgcagttt gccgattcga    1020
ggattcgccc ccaaactatc gcggctgaag accaactcca tgacatgggg atcttttcta    1080
```

| | |
|---|---|
| tcaccagctc cgactctcag gctatgggac gcgtaggcga ggtgatcaca cgcacttggc | 1140 |
| agacagcaga caaaaacaaa aaagagtttg ggcgcttgaa agaggaaaaa ggcgataacg | 1200 |
| acaacttccg catcaaacgc tacatctcta aataccaccat caaccccgcg atcgcgcatg | 1260 |
| ggatttctga ctatgtgggc tctgtggaag tgggcaaata cgccgacctc gtgctttgga | 1320 |
| gtccggcttt ctttggcatt aagcccaata tgattattaa gggcggattt attgcgctct | 1380 |
| ctcaaatggg cgatgccaat gcgtctattc ccacccctca gcccgtctat taccgtgaaa | 1440 |
| tgtttggaca ccatgggaaa aacaaattcg acaccaatat cactttcgtg tcccaagcgg | 1500 |
| cttacaaggc agggatcaaa gaagaactag gctagatcg cgtggtattg ccagtgaaaa | 1560 |
| actgtcgcaa tatcactaaa aaggacctca aattcaacga tgtgaccgca catattgatg | 1620 |
| tcaaccctga aacctataag gtgaaagtgg atggcaaaga ggtaacctct aaagcagcag | 1680 |
| atgaattgag cctagcgcaa ctttataatt tgttctaga | 1719 |

<210> SEQ ID NO 11
<211> LENGTH: 1717
<212> TYPE: DNA
<213> ORGANISM: Helicobacter pylori

<400> SEQUENCE: 11

| | |
|---|---|
| acgcgtatga aaaagattag cagaaaagaa tatgtttcta tgtatggccc tactacaggt | 60 |
| gataaagtga gattgggcga tacagacttg atcgctgaag tagaacatga ctacaccatt | 120 |
| tatggcgaag agcttaaatt cggtggcggt aaaaccctaa gagaaggcat gagccaatct | 180 |
| aacaacccta gcaaagaaga actggatcta atcatcacta acgctttaat cgtggattac | 240 |
| accggtattt ataaagcgga tattggtatt aaagatggca aaatcgctgg cattggtaaa | 300 |
| ggcggtaaca agacatgca agatggcgtt aaaaacaatc ttagcgtggg tcctgctact | 360 |
| gaagccttag ccggtgaagg tttgatcgta actgctggtg gtattgacac acacatccac | 420 |
| ttcatttcac cccaacaaat ccctacagct tttgcaagcg gtgtaacaac catgattggt | 480 |
| ggcggaactg gtcctgctga tggcactaac gcgactacta tcactccagg tagaagaaat | 540 |
| ttaaaatgga tgctcagagc ggctgaagaa tattctatga atttaggttt cttggctaaa | 600 |
| ggtaacgctt ctaacgatgc gagcttagcc gatcaaattg aagccggtgc gattggcttt | 660 |
| aaaattcacg aagactgggg caccactcct tctgcaatca atcatgcgtt agatgttgcg | 720 |
| gacaaatacg atgtgcaagt cgctatccac acagacactt tgaatgaagc cggttgtgta | 780 |
| gaagacacta tggctgctat tgctggacgc actatgcaca ctttccacac tgaaggcgct | 840 |
| ggcggcggac acgctcctga tattattaaa gtagccggtg aacacaacat tcttcccgct | 900 |
| tccactaacc ccaccatccc tttcaccgtg aatacagaag cagagcacat ggacatgctt | 960 |
| atggtgtgcc accacttgga taaaagcatt aagaagatg ttcagttcgc tgattcaagg | 1020 |
| atccgccctc aaaccattgc ggctgaagac actttgcatg acatggggat tttctcaatc | 1080 |
| accagttctg actctcaagc gatgggccgt gtgggtgaag ttatcactag aacttggcaa | 1140 |
| acagctgaca aaaacaagaa agaatttggc cgcttgaaag aagaaaaagg cgataacgac | 1200 |
| aacttcagga tcaaacgcta cttgtctaaa tacaccatta acccagcgat cgctcatggg | 1260 |
| actagcgagt atgtcggttc tgtagaagtg ggcaaagtag ctgacttggt attgtggagt | 1320 |
| ccagcattct ttggcgtgaa acctaacatg atcatcaaag gtgggttcat tgcattaagc | 1380 |
| caaatgggcg atgcgaacgc ttctatccct acccctcaac cggtttatta cagagaaatg | 1440 |
| ttcgctcatc gtggtaaagc taaatacgat gcaaacatca ctttgtgtc tcaagcggct | 1500 |

```
tatgacaaag gcattaaaga agaattagga cttgaaagac aagtgttgcc ggtaaaaaat    1560
tgcagaaaca tcaccaaaaa agacatgcaa ttcaacgaca ctaccgctca cattgaagtc    1620
aatcctgaaa cttaccatgt gttcgtggat ggcaagaag taacttctaa accagctaat     1680
aaagtgagct tggcgcaact ctttagcatt ttctaga                              1717

<210> SEQ ID NO 12
<211> LENGTH: 853
<212> TYPE: DNA
<213> ORGANISM: Rotavirus VP7

<400> SEQUENCE: 12
acgcgtggca ttaaccttcc aattactgga tcaatggaca cggcatatgc aaactcaact     60
caatcggaaa catttctgac ttctacccta tgcctttact atccaaaaga ggcagctact    120
gagataaacg ataactcatg gaaagacacg ctatcgcaac tattcctgac gaaaggatgg    180
ccaacagggt cagtctattt taaagaatac accgacatag cagcattctc agttgatccg    240
caactatact gtgattacaa cgttgtgctg atgaaatatg acgcttcatt gcaaatggat    300
atgtcggagc ttgcggactt gatactgaat gaatggcttt gcaacccaat ggacatcaca    360
ctgtactact atcagcaaac agacgaagca aacaaatgga tatctatggg ttcctcctgt    420
actattaaag tatgtccact taacactcag acgctaggaa taggctgtct cactaccgat    480
gctgcgactt ttgaagaaat tgcgactgcg gagaagttag cgataatgga tgtcgtagat    540
ggcgtaaatc acaaacttga cgttacaact gcgacttgta cgattcgcaa ctgcaagaaa    600
ctcggtccac gggaaaacgt agcagttata caagtaggcg gttctgacgt aatagacata    660
actgcggatc ctacaactgc accacaaacc gagagaatga tgcgcattaa ttggaaaaaa    720
tggtggcaag tgttctatac tgtcgttgat tacgtaaatc agataatttc agcaatgtcc    780
aagcgatctc gatcactgaa ctcagcgact ttttattata gagtgtaggt ataactgaag    840
ttacagctct aga                                                       853
```